(12) United States Patent
Boland, II et al.

(10) Patent No.: US 9,402,649 B2
(45) Date of Patent: Aug. 2, 2016

(54) SYSTEMS AND METHODS FOR PERCUTANEOUS OCCLUSION CROSSING

(71) Applicant: W. L. Gore & Associates, Inc., Newark, DE (US)

(72) Inventors: Brian R. Boland, II, Peoria, AZ (US); Edward H. Cully, Flagstaff, AZ (US); Jeffrey B. Duncan, Flagstaff, AZ (US); Paul D. Goodman, Flagstaff, AZ (US)

(73) Assignee: W.L. GORE & ASSOCIATES, INC., Newark, DE (US)

( * ) Notice: Subject to any disclaimer, the term of this patent is extended or adjusted under 35 U.S.C. 154(b) by 0 days.

(21) Appl. No.: 14/561,033

(22) Filed: Dec. 4, 2014

(65) Prior Publication Data
US 2015/0094747 A1   Apr. 2, 2015

Related U.S. Application Data

(63) Continuation of application No. 13/273,111, filed on Oct. 13, 2011, now Pat. No. 8,932,315.

(60) Provisional application No. 61/394,286, filed on Oct. 18, 2010.

(51) Int. Cl.
*A61B 17/34* (2006.01)
*A61B 17/3207* (2006.01)
(Continued)

(52) U.S. Cl.
CPC ............ *A61B 17/3207* (2013.01); *A61B 17/22* (2013.01); *A61M 25/0054* (2013.01);
(Continued)

(58) Field of Classification Search
CPC .............. A61B 17/3207; A61B 2017/00309; A61B 2017/00867; A61B 2017/22042; A61B 2017/22044; A61B 2017/22077; A61B 2017/22094; A61B 2017/22095; A61M 2025/0197; A61M 25/0082; A61M 25/0194
USPC .......................................... 606/159, 167, 185
See application file for complete search history.

(56) References Cited

U.S. PATENT DOCUMENTS

| 4,552,554 A | 11/1985 | Gould et al. |
| 4,774,949 A | 10/1988 | Fogarty |

(Continued)

FOREIGN PATENT DOCUMENTS

| WO | 93/05841 | 4/1993 |
| WO | 96/27330 | 9/1996 |

(Continued)

OTHER PUBLICATIONS

Bolia A, Nasim A, Bell PRF. Percutaneous Extraluminal (Subintimal) Recanalization of a Brachial Atery Occlusin Following Cardiac Catheterization. Cardio Vasc Intervent Radiol 1996; 19:184-186.

(Continued)

*Primary Examiner* — Katherine M Shi

(57) ABSTRACT

The present invention provides methods and apparatuses for crossing or bypassing total or near total occlusions of vessels through the use of elongate members and specialized catheters that include a piercing catheter, a reentry catheter, a multi-lumen, reentry catheter, and combinations thereof. A piercing catheter comprises a distal tip used to pierce an occlusion in a crossing procedure and can be configured to microdissect the occlusion or provide support for an elongate member. A reentry catheter comprises a distal side port and ramp to facilitate the reentry or perforation of a vessel wall. A multi-lumen, reentry catheter comprises a tearable lumen divider and a distal side port and ramp.

8 Claims, 22 Drawing Sheets

(51) Int. Cl.
  *A61B 17/22* (2006.01)
  *A61M 25/00* (2006.01)
  *A61M 25/01* (2006.01)
  *A61B 17/00* (2006.01)

(52) U.S. Cl.
  CPC ....... *A61M25/0082* (2013.01); *A61M 25/0194* (2013.01); *A61B 2017/00309* (2013.01); *A61B 2017/00867* (2013.01); *A61B 2017/22042* (2013.01); *A61B 2017/22044* (2013.01); *A61B 2017/22077* (2013.01); *A61B 2017/22094* (2013.01); *A61B 2017/22095* (2013.01); *A61M 2025/0197* (2013.01)

(56) References Cited

U.S. PATENT DOCUMENTS

| | | |
|---|---|---|
| 4,898,575 A | 2/1990 | Fischell et al. |
| 5,243,997 A | 9/1993 | Uflacker et al. |
| 5,364,376 A | 11/1994 | Horzewski et al. |
| 5,389,087 A | 2/1995 | Miraki |
| 5,538,504 A | 7/1996 | Linden et al. |
| 6,190,353 B1 | 2/2001 | Makower et al. |
| 6,231,546 B1 | 5/2001 | Milo et al. |
| 6,283,983 B1 | 9/2001 | Makower et al. |
| 6,302,875 B1 | 10/2001 | Makower et al. |
| 6,375,615 B1 | 4/2002 | Flaherty et al. |
| 6,464,665 B1 | 10/2002 | Heuser |
| 6,511,458 B2 | 1/2003 | Milo et al. |
| 6,719,725 B2 | 4/2004 | Milo et al. |
| 6,726,677 B1 | 4/2004 | Flaherty et al. |
| 6,746,462 B1 | 6/2004 | Selmon et al. |
| 7,004,173 B2 | 2/2006 | Sparks et al. |
| 7,179,270 B2 | 2/2007 | Makower |
| 7,648,517 B2 | 1/2010 | Makower et al. |
| 2002/0143358 A1 | 10/2002 | Domingo et al. |
| 2003/0236542 A1 | 12/2003 | Makower |
| 2004/0158143 A1 | 8/2004 | Flaherty et al. |
| 2005/0033236 A1 | 2/2005 | Wijay et al. |
| 2005/0171478 A1 | 8/2005 | Selmon et al. |
| 2005/0267458 A1 | 12/2005 | Paul et al. |
| 2006/0094930 A1 | 5/2006 | Sparks et al. |
| 2006/0241342 A1 | 10/2006 | Macaulay et al. |
| 2007/0010840 A1 | 1/2007 | Rosenthal et al. |
| 2007/0083215 A1 | 4/2007 | Hamer et al. |
| 2007/0088230 A1 | 4/2007 | Terashi et al. |
| 2007/0093781 A1 | 4/2007 | Kugler et al. |
| 2007/0265563 A1 | 11/2007 | Heuser |
| 2009/0054875 A1 | 2/2009 | Strauss et al. |
| 2009/0088685 A1 | 4/2009 | Kugler et al. |
| 2009/0163872 A1* | 6/2009 | Tekulve .................. 604/164.11 |
| 2009/0281564 A1 | 11/2009 | Kontos |
| 2009/0287114 A1 | 11/2009 | Lee et al. |
| 2011/0144677 A1 | 6/2011 | Ward et al. |

FOREIGN PATENT DOCUMENTS

| | | |
|---|---|---|
| WO | 97/13463 | 4/1997 |
| WO | 01/22887 | 4/2001 |
| WO | 2008/006111 | 1/2008 |
| WO | 2009/100129 | 8/2009 |

OTHER PUBLICATIONS

Bolia A, et al. Percutaneous Transluminal Angioplasty of Occlusions of the Femoral and Popliteal Arteries by Subintimal Dissection. Cardio Vasc Intervent Radiol, 1990, vol. 13, 6: 357-363.

* cited by examiner

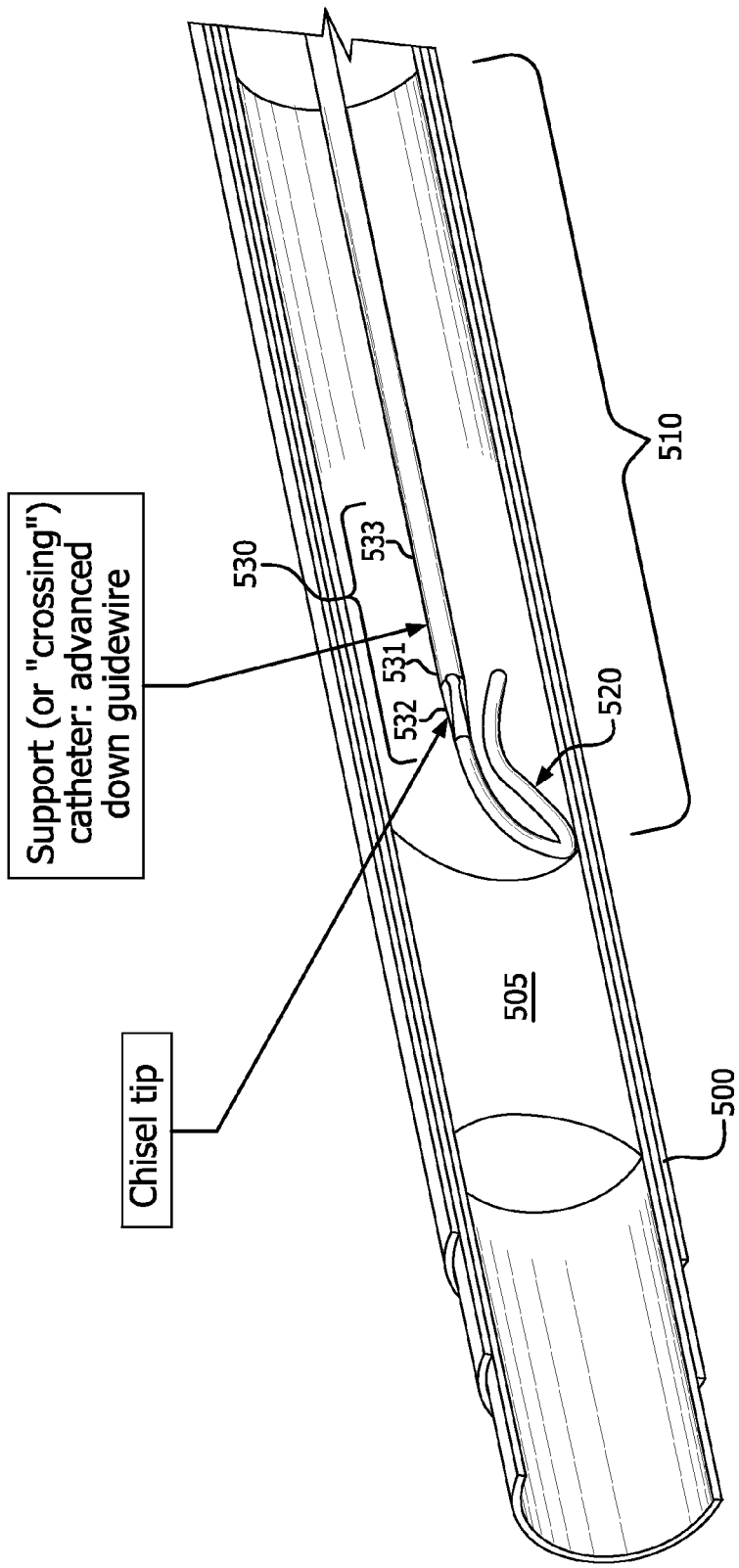

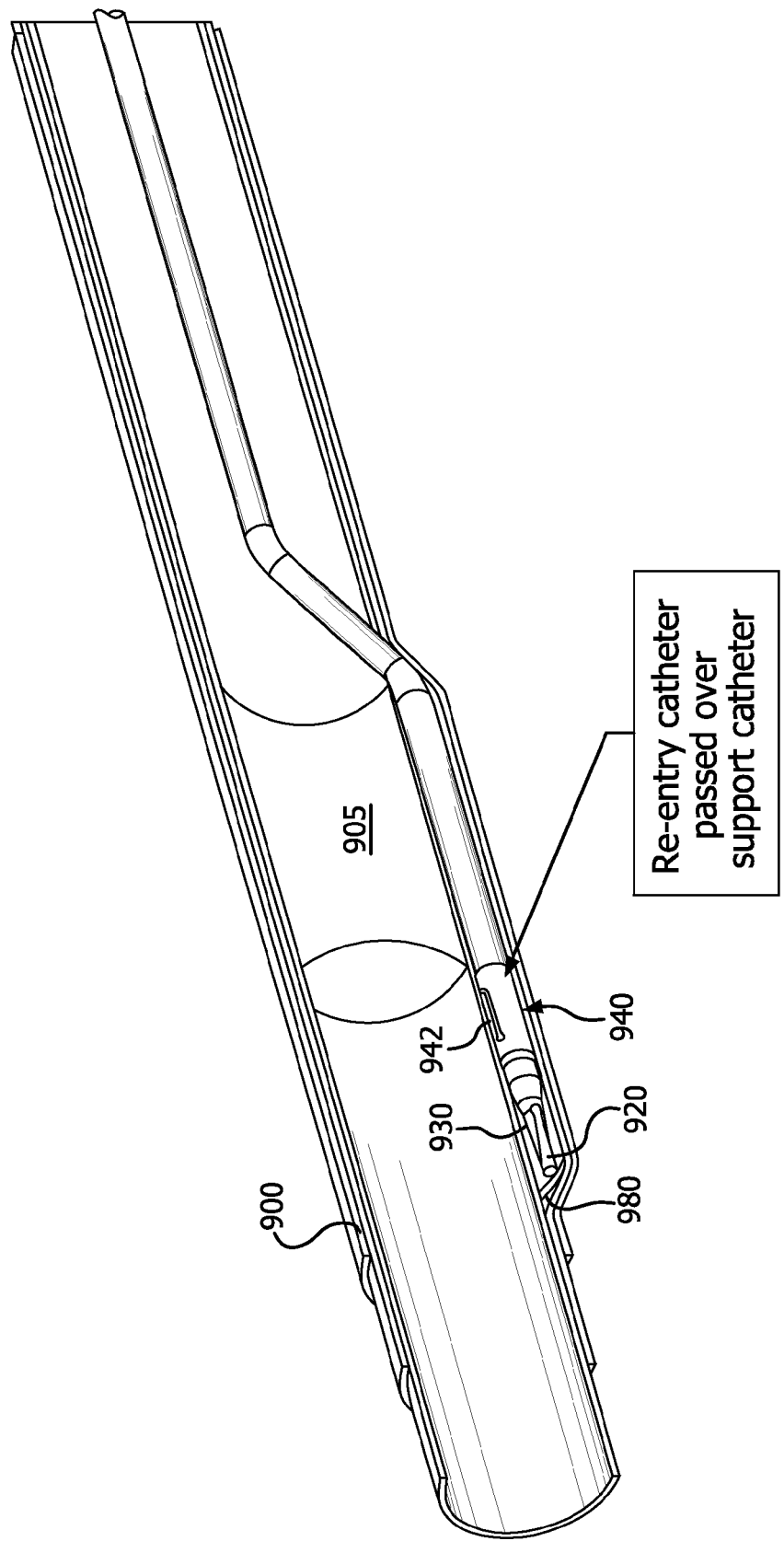

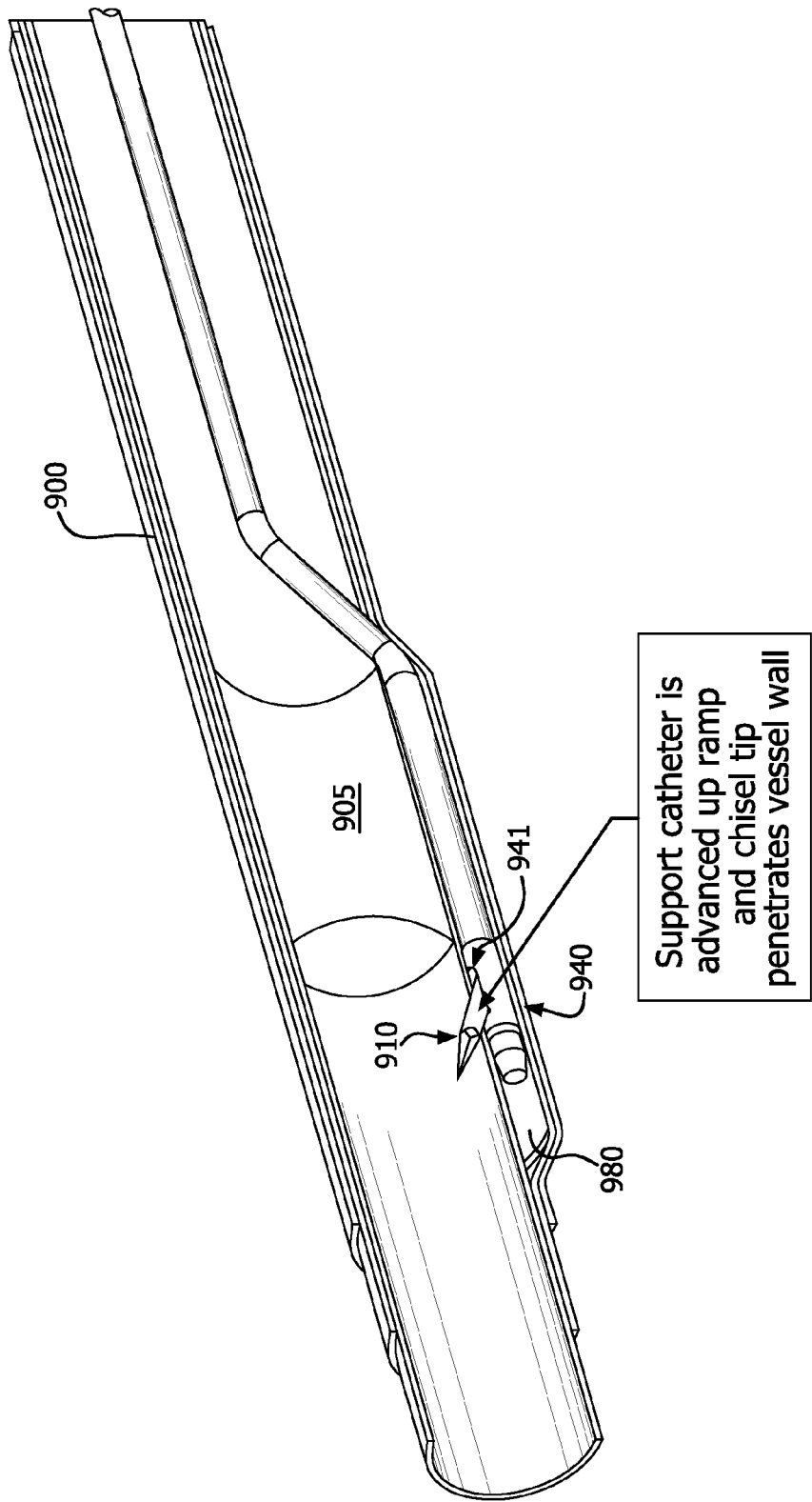

SYSTEMS AND METHODS FOR PERCUTANEOUS OCCLUSION CROSSING

FIELD OF THE INVENTION

The present invention generally relates to the field of endoluminal products, and more particularly, to the field of percutaneous occlusion crossing systems and methods.

BACKGROUND

Cardiovascular disease, including atherosclerosis, is a leading cause of death in the United States. One method for treating atherosclerosis and other forms of vessel lumen narrowing is angioplasty. The objective of angioplasty is to restore adequate blood flow through the affected vessel, which may be accomplished by introducing a treatment catheter within the narrowed lumen of the vessel to dilate it.

The anatomy of vessels varies widely from patient to patient. Often a patient's vessels are irregularly shaped, highly tortuous and very narrow. The tortuous configuration of the vessels may present difficulties to a clinician in advancement of a treatment catheter to a treatment site. In addition, in some instances, the extent to which the lumen is narrowed at a treatment site is so severe that the lumen is completely or nearly completely obstructed, which may be described as a total occlusion. A chronic total occlusion (CTO) is generally an occlusion that has completely blocked a blood vessel for an extended period of time.

The tissue composition of a CTO is generally a variable mix of collagen-rich plaque, layered thrombus, calcium, and inflammatory cells with fibro-calcific caps at both ends. This fibrous cap may present a surface that is difficult to penetrate with a conventional medical guidewire such that one method of crossing a CTO includes utilizing a stiffer guidewire to create a new channel through the occlusion. Due to the fibrous cap of the CTO, a stiffer guidewire still may not be able to cross it and the distal end of the guidewire may buckle or prolapse within the vessel when force is applied. In addition, a clinician must take care to avoid perforation of the vessel wall when using a stiffer guidewire.

By way of mere examples, CTOs are often defined as coronary occlusions that have had thrombolysis in myocardial infarction (TIMI) grade flow of 0 or 1 for an estimated duration of at least one month. Available interventional procedures to treat coronary occlusions include coronary angioplasty, e.g., percutaneous transluminal coronary angioplasty (PTCA), and stent placement, e.g., drug-eluting stent placement. These procedures are considered percutaneous because they are performed through a tube or catheter inserted into a blood vessel, rather than through an incision in the chest. However, coronary artery CTOs have historically been some of the most challenging types of blockages to treat with percutaneous interventional procedures because the fibrotic and calcified nature of the CTOs makes passage difficult. As a result, many patients with coronary artery CTOs require coronary artery bypass graft (CABG) surgery to treat the blockage. CTOs are also frequently present in many other locations of the human vascular system, including in peripheral vessels.

Therefore, a need exists to develop better systems and methods for percutaneous treatment of occlusions, especially with respect to improving the available systems and methods for penetrating and bypassing the occlusion or anatomical blockage, and for incorporating multiple options to recanalize the vessel within a single device.

SUMMARY OF THE INVENTION

In accordance with exemplary embodiments, the present invention comprises systems and methods for penetrating and bypassing chronic total or near total occlusions of vessels through the use of elongate members and specialized catheters, for example, piercing catheters, reentry catheters, and multi-lumen, reentry catheters. The systems and methods described herein may be useful in connection with the treatment of coronary artery disease, peripheral vascular diseases, portal hypertension, carotid artery disease, renal vascular hypertension, subintimal angioplasty, biopsies, in situ fenestration of other tissues, amongst other conditions affecting anatomical conduits. The present invention may also be useful to pierce grafts or stent-grafts to create fenestrations and to create anatomical passages such as an arterio-venous fistula.

In accordance with an exemplary embodiment of the present invention, a piercing catheter having a distal tip is configured to pierce and thereby cross an occlusion. In accordance with an aspect of this exemplary embodiment, the piercing catheter is configured to perform micro-dissection to cross the occlusion.

Another embodiment of the present invention comprises a reentry catheter having a side-port and ramp to guide reentry of an inner elongate member from the sub-intimal space following sub-intimal dissection. In an embodiment, upon withdrawing the inner elongate member to the proximal side of the side-port and ramp, the ramp is actuated to direct the inner elongate member through the side-port for reentry into the vessel from the sub-intimal space upon subsequently advancement of the inner elongate member.

Yet another embodiment of the present invention comprises a multi-lumen reentry catheter having a side-port and ramp to guide reentry of an inner elongate member from the sub-intimal space following sub-intimal dissection. In an embodiment, the reentry catheter lumens are separated by a tearable sheath which supports the ramp in a partially actuated configuration. The ramp is fully actuated by advancing the inner elongate member sufficient to tear the tearable sheath and thereby remove the support for the ramp, whereupon the inner elongate member can be withdrawn to allow full actuation and then advanced through the side-port for reentry into the vessel's true lumen from the sub-intimal space.

In yet another embodiment, a single device has the capabilities to perform a piercing procedure and a reentry procedure, by incorporating a piercing catheter and a reentry catheter into a single device.

Exemplary methods are also described herein.

Persons skilled in the art will appreciate the embodiments described herein may be useful in connection with crossing or creating one or more ducts through a wide variety of anatomical features.

BRIEF DESCRIPTION OF THE DRAWINGS

The exemplary embodiments of the present invention will be described in conjunction with the accompanying drawing figures in which like numerals denote like elements and:

FIGS. 5a-5c illustrate a method of the present invention for crossing an occlusion within a vessel;

FIG. 6 illustrates an enlarged view of a hollow chisel embodiment in which an elongate member occupies the lumen and positioning the chisel tip such that it is radially spaced apart from the position illustrated in FIG. 4a;

FIG. 9c illustrates the reentry catheter passed over the piercing catheter;

FIG. 9f illustrates the piercing catheter advanced up the ramp after penetrating the vessel wall distal the occlusion;

DETAILED DESCRIPTION

Figure 1:
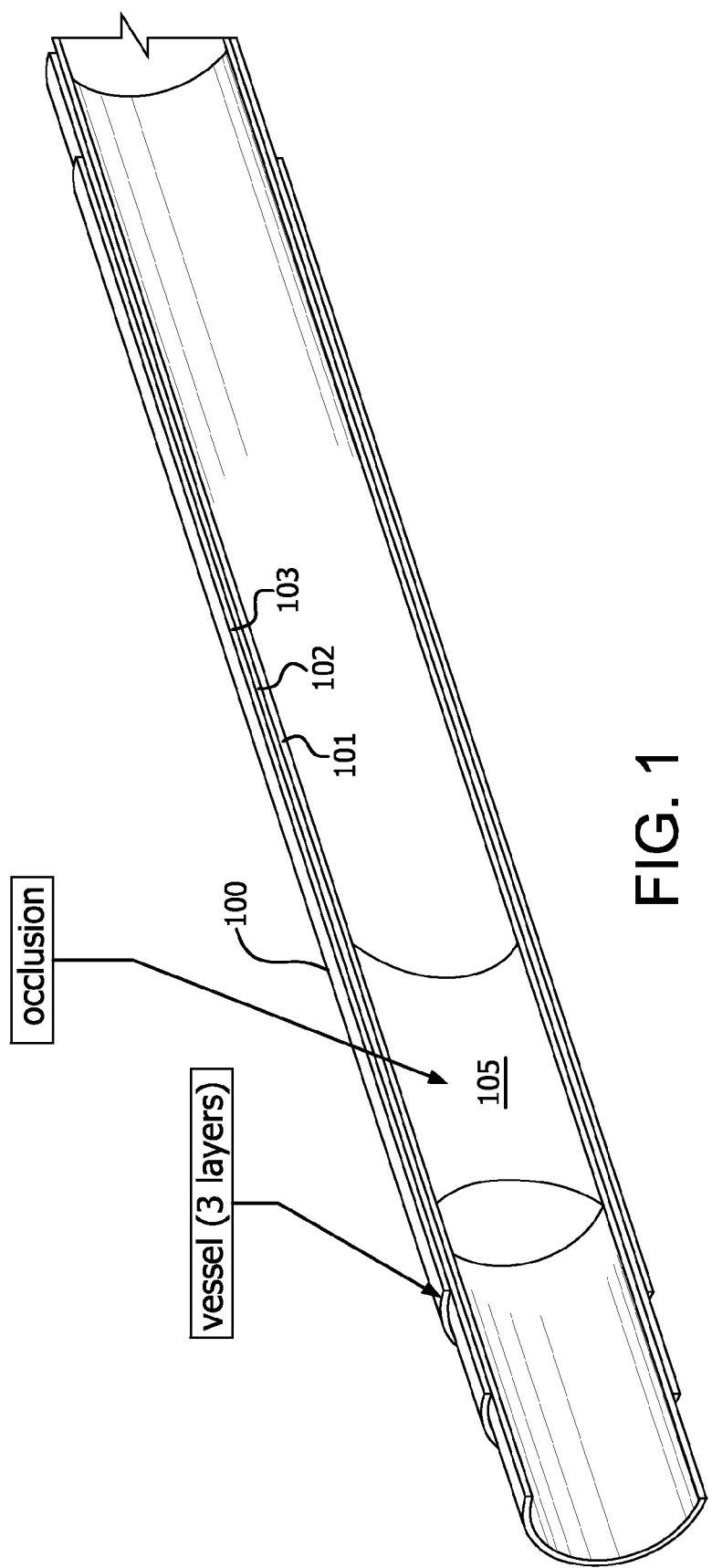
FIG. 1 is a cross-sectional view of an occluded vessel showing the three vessel layers.

Persons skilled in the art will readily appreciate that various aspects of the present invention may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present invention, and in that regard, the drawing figures should not be construed as limiting. Finally, although the present invention may be described in connection with various principles and beliefs, the present invention should not be bound by theory.

In accordance with exemplary embodiments, the present invention comprises systems and methods for penetrating and bypassing chronic total or near total occlusions of vessels through the use of elongate members and specialized catheters, for example, piercing catheters, reentry catheters, and multi-lumen, reentry catheters. The systems and methods described herein may be useful in connection with the treatment of coronary artery disease, peripheral vascular diseases, portal hypertension, carotid artery disease, renal vascular hypertension, amongst other conditions affecting anatomical conduits. The present invention may also be useful to pierce grafts or stent-grafts to create fenestrations and to create anatomical passages such as an arterio-venous fistula.

As used herein, a "vessel" may be an artery, vein, capillary or the like, or any other anatomical passageway or conduit existing in a healthy subject. As used herein, an "occlusion" may be a total (e.g., a CTO), near total or partial blockage of a vessel. Turning to the drawing figures, FIG. 1 is a cross-sectional view of an exemplary vessel 100 having an occlusion 105 and having multiple layers 101, 102, and 103, which may correspond to the intima, media, and adventitia layers respectively.

Figure 2:
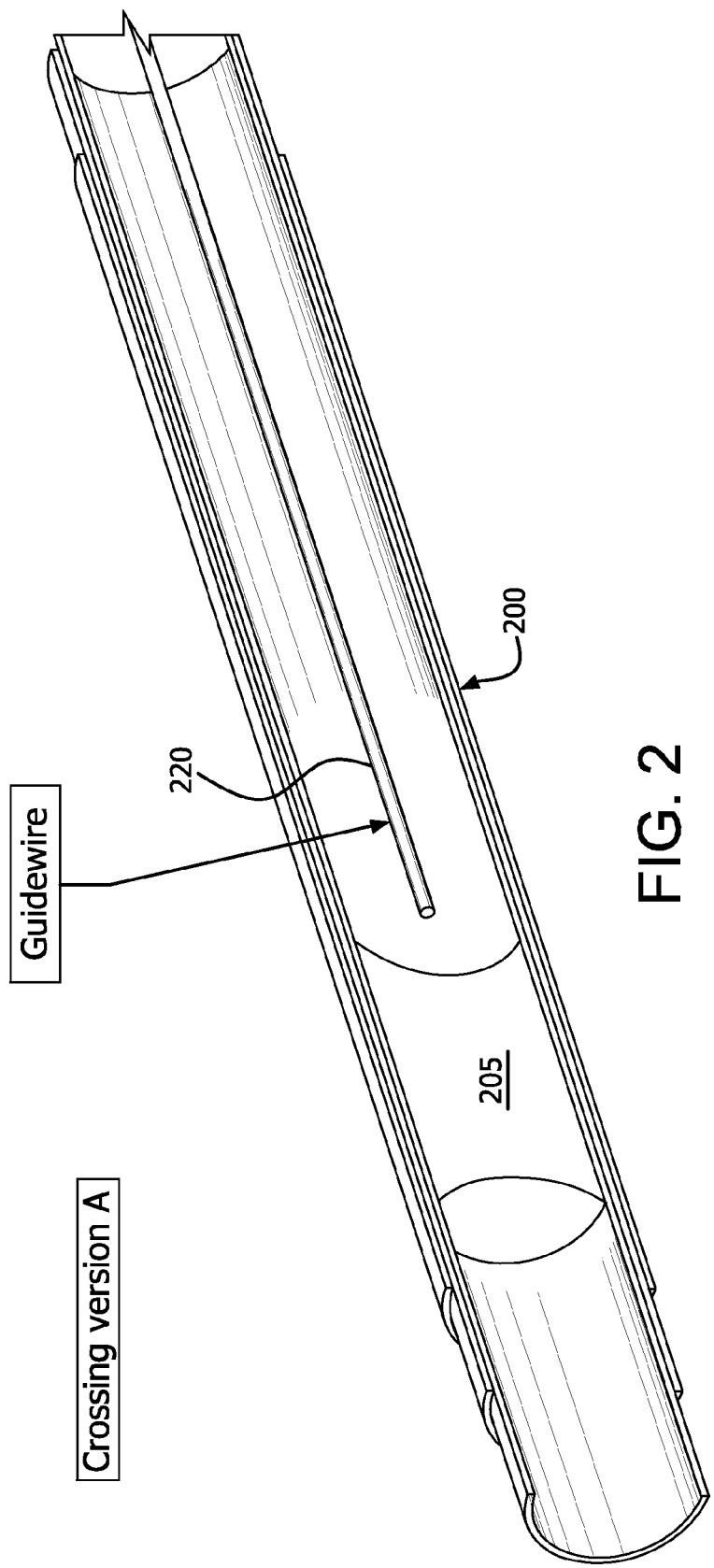
FIG. 2 illustrates an elongate member approaching an occlusion in a vessel.

As used herein, an "elongate member" is a flexible element having proximal and distal ends and capable of passing through a tortuous vessel, such as a guidewire, catheter, optical fiber, or the like. An exemplary elongate member may comprise a blunt, rounded, or tapered distal tip, to name a few, and may be characterized by varying degrees of stiffness and/or softness, which may further vary along the length of the elongate member. An exemplary elongate member, or any portion thereof, can be hydrophilic or hydrophobic. Additionally, an exemplary elongate member, or any portion thereof, can be comprised of any number of materials including silicone, latex, polyurethane, polyvinyl chloride, polyethylene, nylon, PTFE, ePTFE, stainless steel, nitinol, or any other biocompatible material, including combinations of the foregoing. Said elongate member can be a guidewire, a catheter, or fiber. In one embodiment, said elongate member is a guidewire. In another embodiment said guidewire can be placed into hollow member 333 (FIG. 3) via "over the wire" or by "rapid exchange". Turning back to the drawing figures, FIG. 2 illustrates an elongate member 220 approaching an occlusion 205 in a vessel 200.

Figure 3:
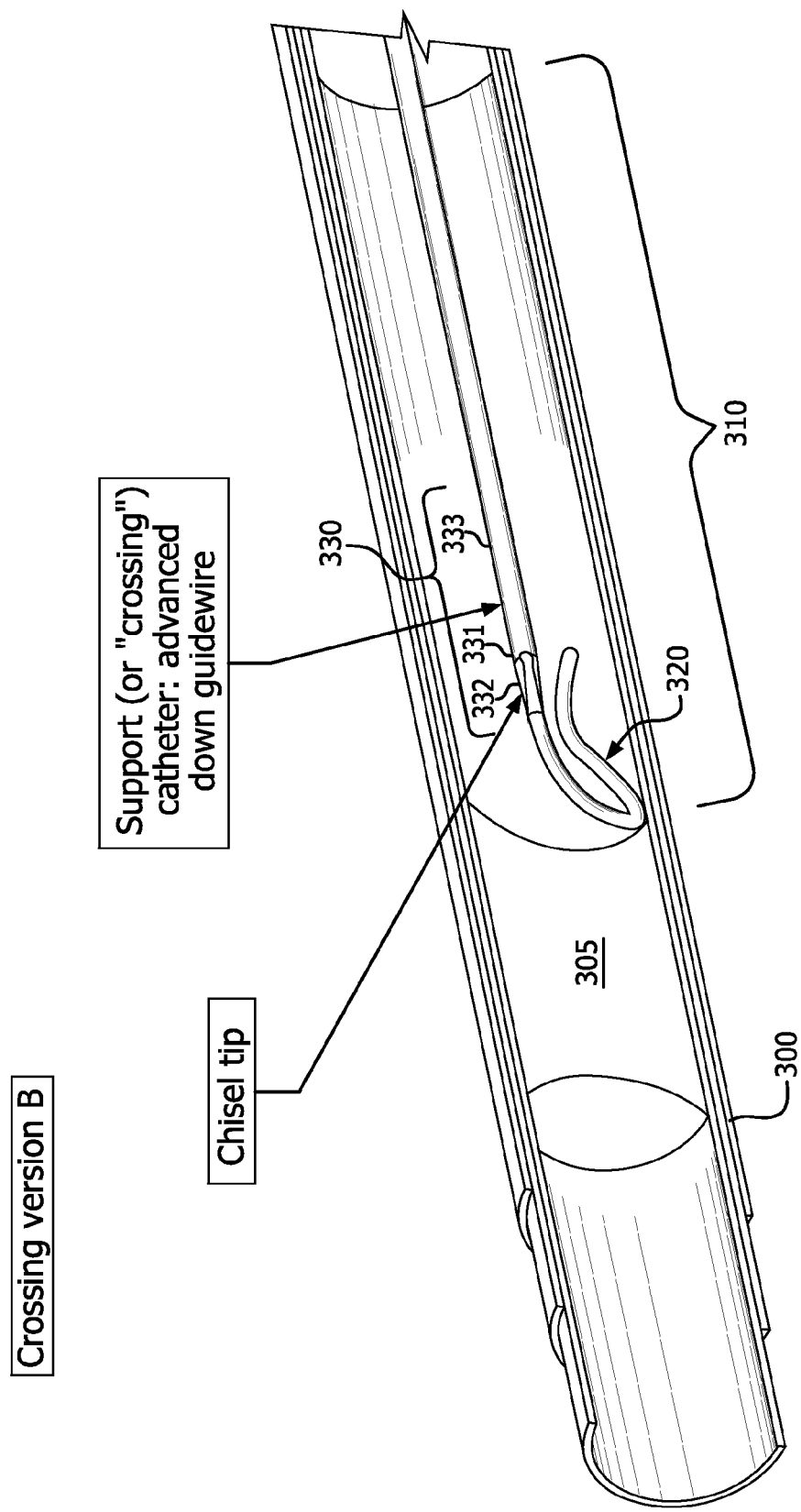
FIG. 3 illustrates an embodiment of a piercing catheter advancing down an elongate member.
Figure 7:
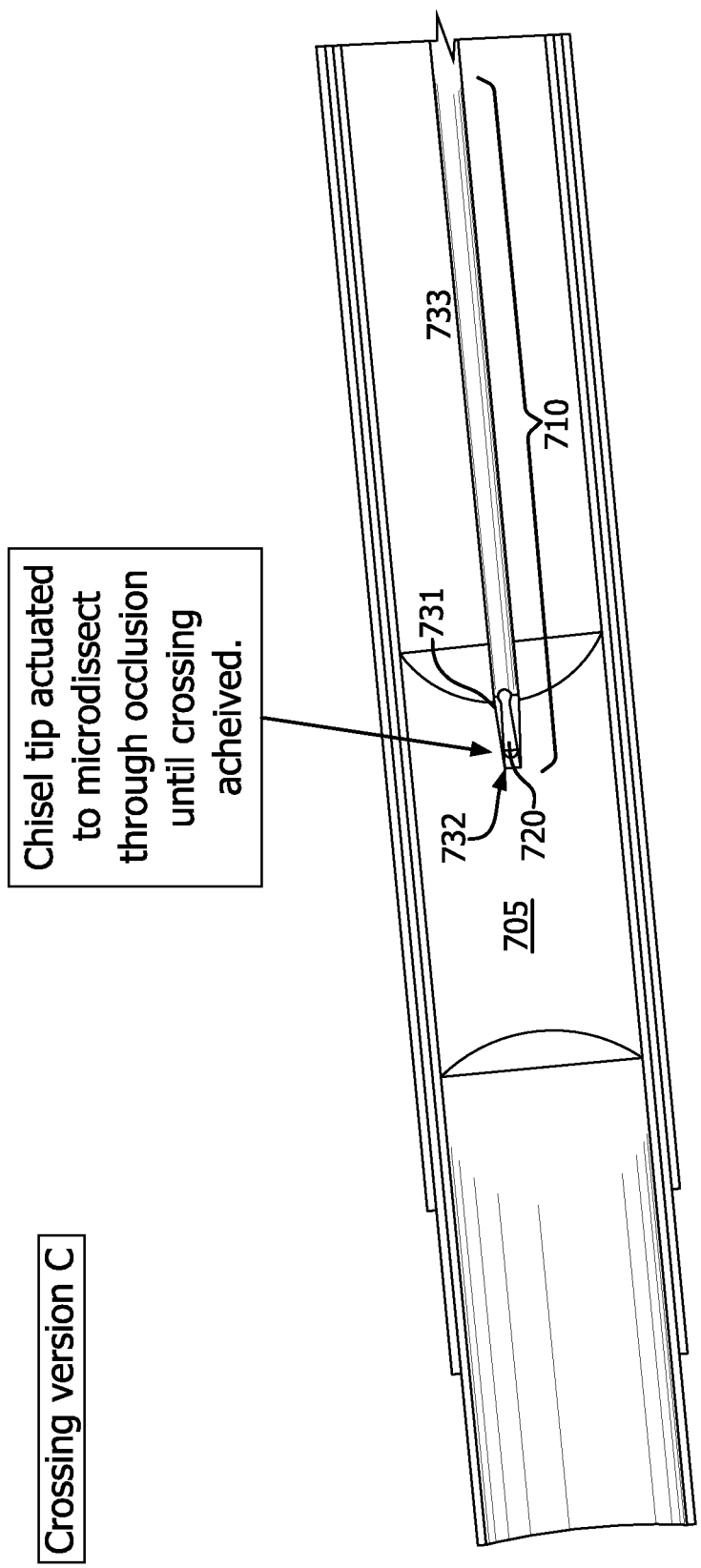
FIG. 7 illustrates a method of the present invention for crossing the occlusion through micro-dissection.

In accordance with an exemplary embodiment, and with reference to FIG. 3, a piercing system 310 (also 510 and 710 in FIGS. 5 and 7 respectively) comprises an elongate member 320 slidably housed within and supported by a piercing catheter 330. Piercing system 310 may be structurally and/or materially configured to cross an occlusion 305 within a vessel 300 by applying a continuous or intermittent longitudinal force or rotational (torquing) movement at the proximal end of at least one of elongate member 320 and piercing catheter 330. For instance, in exemplary embodiments, piercing catheter 330 is configured to pierce and penetrate occlusion 305. That is, and as will be discussed below, in some embodiments, piercing catheter 330 has a shape and/or stiffness sufficient to pierce and penetrate occlusion 305 (or alternatively, through vessel walls), while in other embodiments, piercing catheter 330 is configured to microdissect occlusion 305. For a point of reference, FIG. 7 illustrates an exemplary embodiment of a piercing catheter microdissecting an occlusion.

Figure 4A:
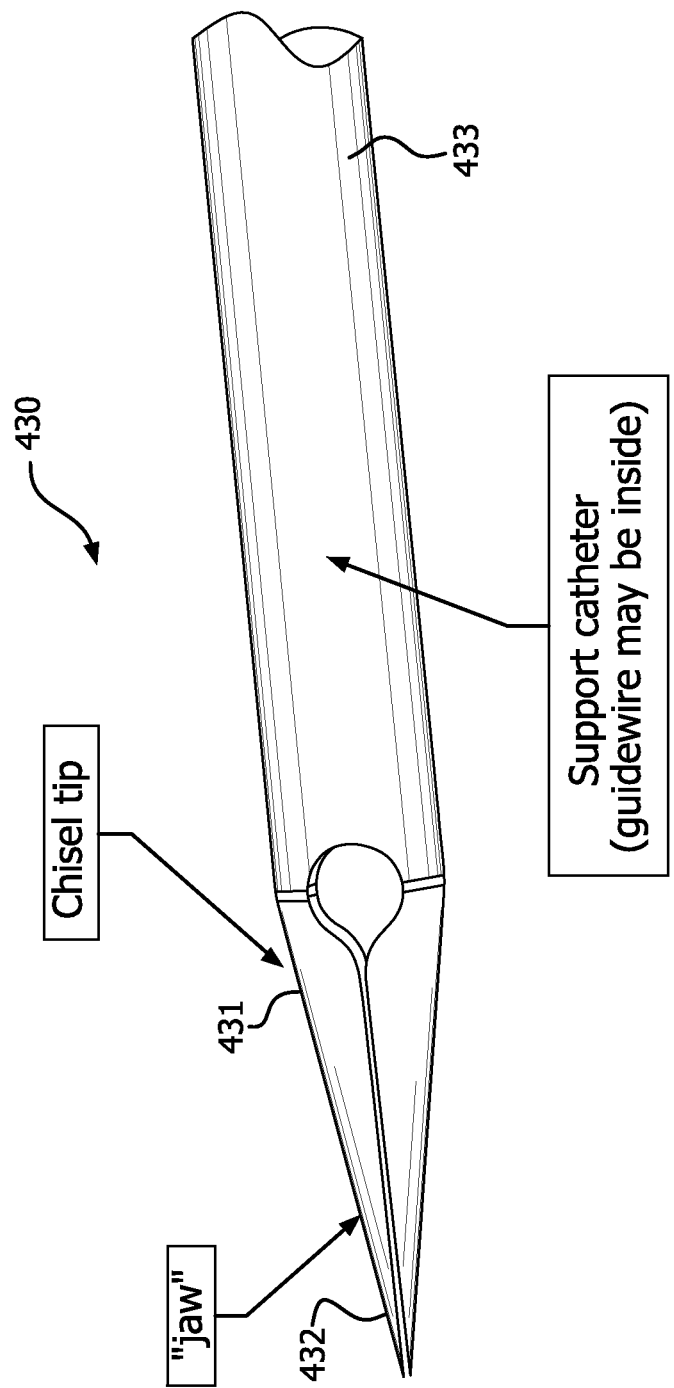
FIGS. 4a-4c illustrate an enlarged view of a hollow chisel in a position in which the tip is proximate the axis, and two views of a cut pattern for strain relief for the hollow member, respectively.
Figure 6:
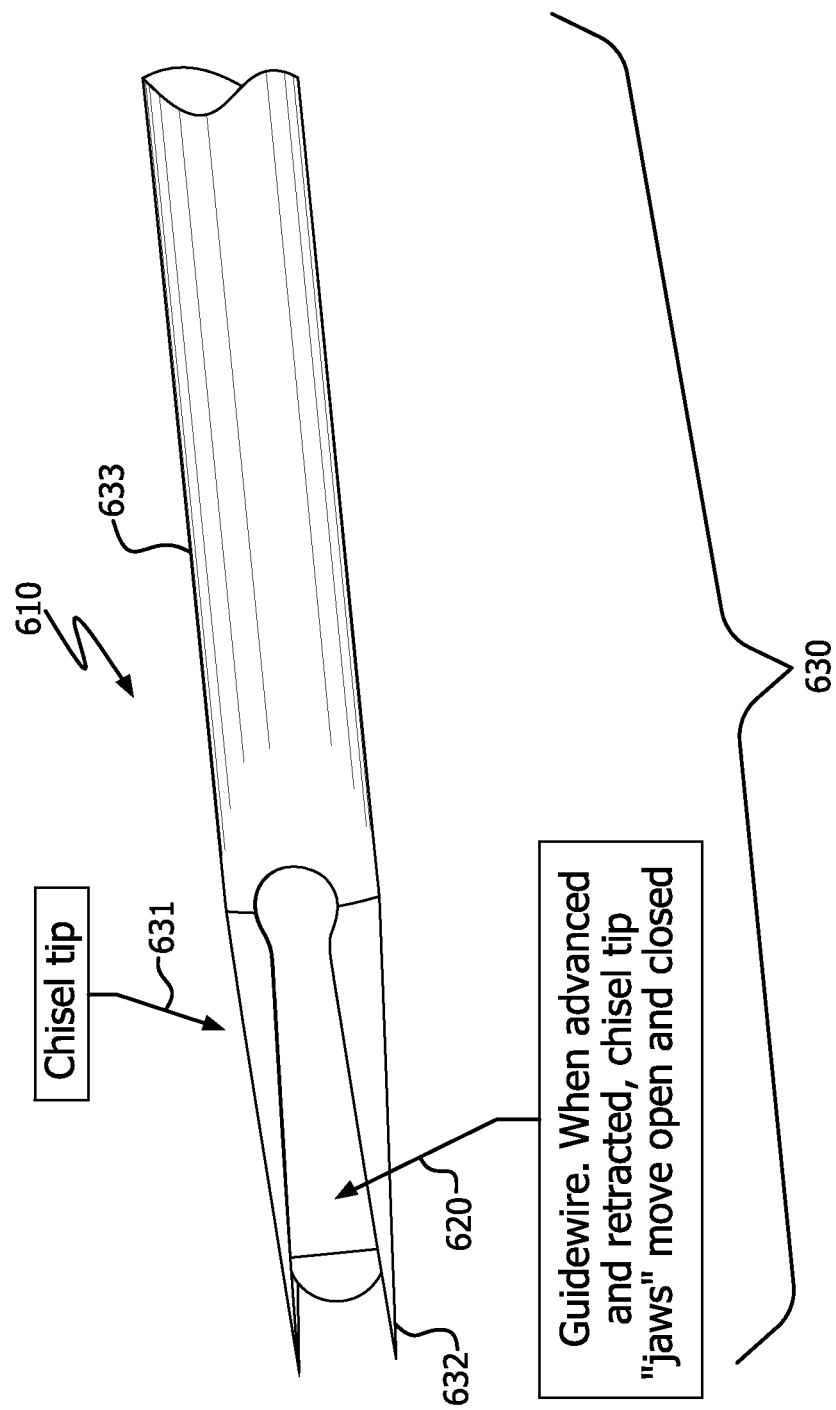

In accordance with an exemplary embodiment, and with continued reference to FIG. 3, piercing catheter 330 may comprise a hollow chisel 331 having a tip 332 and being coupled to the distal end of a hollow member 333. Briefly, as used herein, "hollow" means a passage or space therein which can allow the passage of another object. In accordance with various aspects of this exemplary embodiment, a plurality of hollow chisel 331, tip 332 and hollow member 333 may be comprised of the same material (e.g., cut from a single tube or formed in a common mold). Moreover, any of hollow chisel 331, tip 332 and hollow member 333 and/or the piercing catheter 330 may be coated with an ePTFE film. In exemplary embodiments, elongate member 320 is slidably housed within and supported by hollow member 333. In exemplary embodiments, elongate member 320 is axially movable along the longitudinal axis of hollow member 333 and hollow chisel 331 such that tip 332 is laterally displaced by axial displacement of elongate member 320, for instance, axial displacement on the order of 1 mm. For example, tip 332 may be laterally displaced (e.g., opened and closed or any position in between) in response to selective axial displacement of elongate member 320, between a first position, in which tip 332 is disposed proximal to the axis, and a second position, in which tip 332 is generally radially spaced apart from the first position. For point of reference, FIG. 6 illustrates an embodiment 630 with the hollow chisel 631 and tip 632 of hollow member 633 in a second position (with elongate member 620 moved distally) and FIG. 4a illustrates an embodiment 430 with the tip 432 in a first position.

In exemplary embodiments, hollow member 333 is an elongate member, as that term has been defined herein, configured to house elongate member 320 along its longitudinal axis. The outer diameter of hollow member 333 should permit its passage through lumen of vessel 300 and the inner diameter of hollow member 333 should permit passage of elongate member 320. In exemplary embodiments, the outer diameter of hollow member 333 is from about 0.015 to about 0.055 inches, more preferably from about 0.025 to about 0.045 inches, and most preferably about 0.035 inches. In exemplary embodiments, the inner diameter of hollow member 333 is from about 0.006 to about 0.022 inches, more preferably from about 0.010 to about 0.016 inches, and most preferably about 0.016 inches.

In accordance with exemplary embodiments of the present invention, hollow chisel 331 is coupled to the distal end of hollow member 333. The coupling may occur at or near the point of articulation of tip 332 or further down a chisel shaft (not shown) of hollow chisel 331. In accordance with an aspect of an exemplary embodiment comprising a chisel shaft, an outer surface of the chisel shaft may be spiral-cut for added flexibility, for example, starting at from about 2 to about 3 mm proximal to the point of articulation of tip 332. The dimensions of hollow chisel 331 at its proximal end may be larger or smaller than the dimensions of hollow member 333 at its distal end. That being said, in a preferred embodiment, the diameters are substantially the same to generally align the longitudinal axes for elongate member 320 to travel.

Figure 4B:
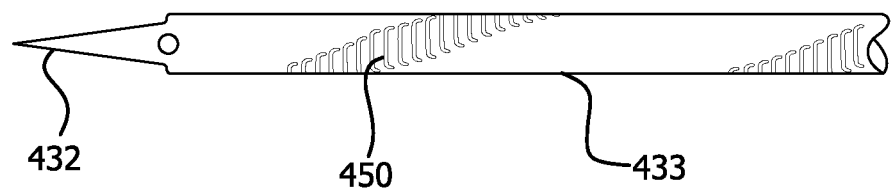
Figure 4C:
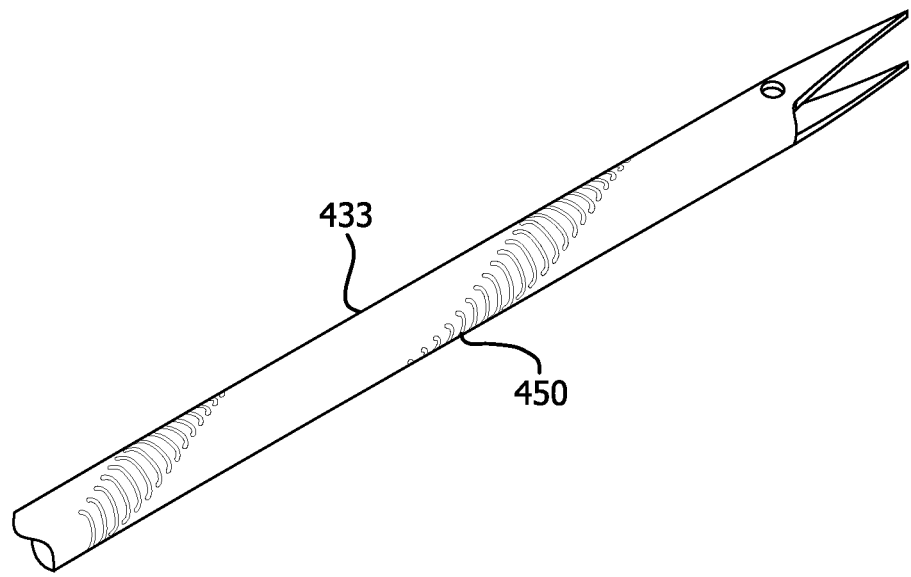

In accordance with exemplary embodiments of the present invention is illustrated by FIG. 4b. In this embodiment, flexibility of the distal region of the hollow member 433 has been improved by cutting openings through hollow member 433. Several cut patterns can be used. In one embodiment, the cut pattern is a series of semi-circular kerfs 450 laid out in a helical pattern on the distal end of the catheter. In another embodiment, length of the semi-circular kerfs 450 is shortened toward the proximal end of the helical pattern. This serves as a strain relief. Several other cut shapes are possible. These include straight kerfs and rectangular or partial rectangular kerfs. It is possible to wrap the cut region with film to allow passage of contrast fluid through hollow member and out its distal end (or out some of kerfs 450 if they are left unwrapped). The film wrap does not hinder the flexibility created by the cuts. In one embodiment said film comprises ePTFE. Flexibility of hollow member 433 may be altered (alone or in combination with placement of kerfs 450) by varying the wall thickness of member 433 and/or varying the thermal treatment applied to hollow member. As is known in the art, heat treatment of metals may alter their flexibility. In various embodiments, tip 432 may possess different shapes. For example, tip 432 may feature a pointed terminal end such as that shown in FIG. 4a. In certain embodiments, tip 432 may have a more rounded end. In various embodiments, hollow member 433 may comprise different shaped terminal ends on both its ends. Such configurations allow the clinician to choose tip end shape or change the tip used during a procedure by removing hollow member 433 and inserting the opposite end of hollow member 433.

In various embodiments, tip 332 comprises one or a plurality of separate elements at its distal end, at least one of which is moveable in response to selective axial displacement of elongate member 320. For example, tip 332 may comprise one, two, three, four, five, six or any other suitable number of separate elements at its distal end. For the avoidance of doubt, such separate elements may emanate from a unitary structure such as a ring at or near its proximal end. Tip 332 itself may be generally smooth or modified with serrations, barbs, hooks, anchors or the like.

In different embodiments, tip 332 may taper or otherwise come to a sharp point, a straight wedge, a curved wedge, or any other end that facilitates piercing and/or penetrating occlusion 305. Tip 332 may be comprised of a shape memory material such as nitinol to facilitate its articulation. In exemplary embodiments, the shape memory material may permit the tip to regain its closed position form after withdrawal of elongate member 320 from its lumen. Other modes of tip reformation could be through a spring-loaded micro hinge, a collapsible mesh, or any other structures which permit the tip to regain its closed position form upon withdrawal of elongate member 320 from its lumen. In another embodiment, said shape memory alloy is selected from the group consisting of spring steel, Eligloy and carbon fiber composite.

In exemplary embodiments, tip 332 is biased in a closed position when elongate member 320 is withdrawn out of the lumen of hollow chisel 331. In related embodiments, elongate member 320 is reciprocated in and out of the lumen of hollow chisel 331 to articulate tip 332 between a closed tip and an open tip configuration, for example, to perform micro-dissection. The closed and open configurations could alternate between a sharp tip and a blunt tip, respectively, or any shaped tip which facilitates micro-dissection. In one embodiment, said elongate member is reciprocated manually or automatically using a device that attaches to the elongate member and reciprocates said elongate member.

Exemplary embodiments of the present invention provide reentry systems configured to bypass an occlusion. Similarly, exemplary embodiments of the present invention provide reentry systems configured to cross an occlusion as described above, and also to bypass an occlusion in the event crossing by piercing and penetrating is unsuccessful. Bypassing an occlusion in exemplary embodiments comprises sub-intimal dissection. In general, embodiments of the present invention may facilitate initial entry or reentry of an elongate member into a vessel or other anatomical feature.

Figure 8:
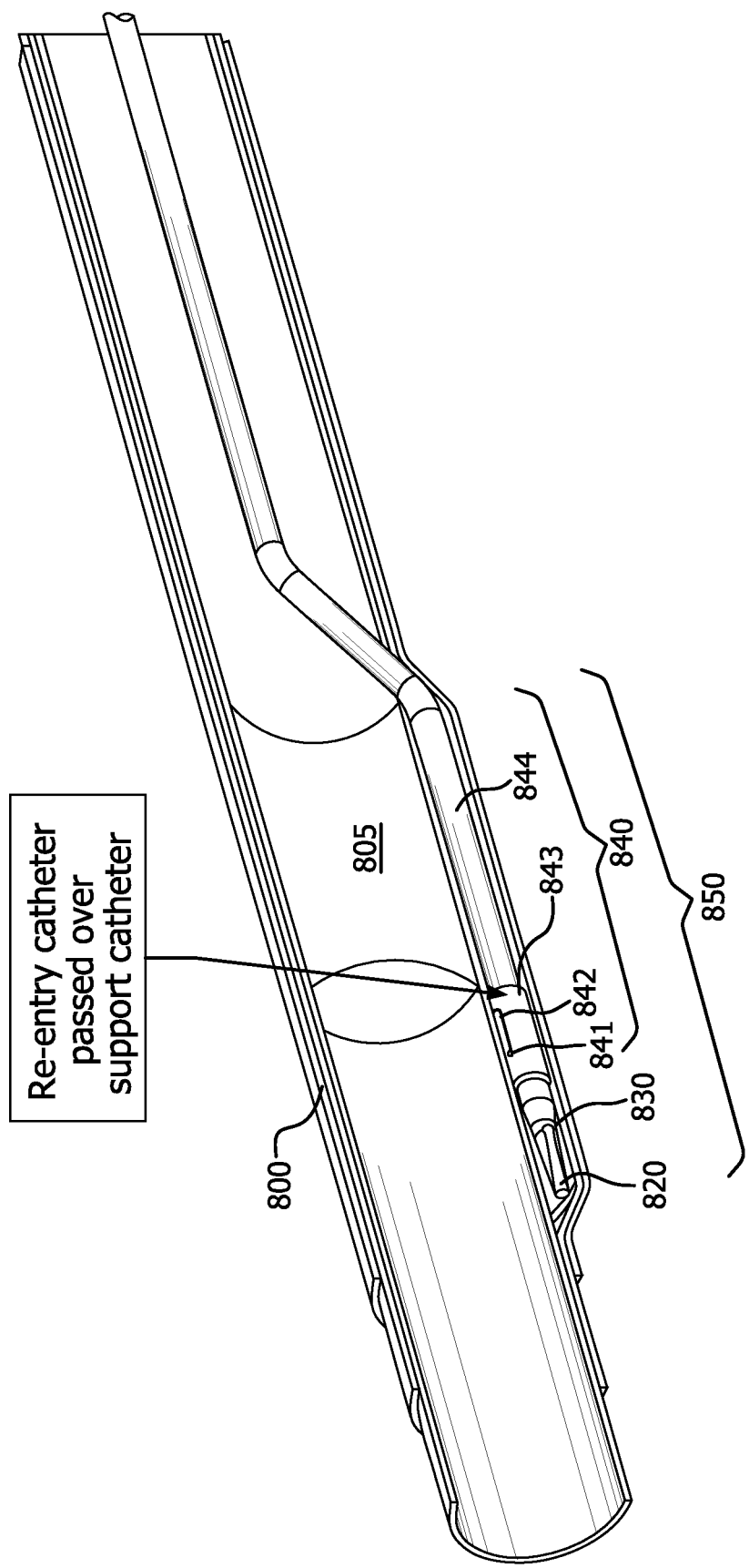
FIG. 8 illustrates an embodiment of a reentry-crossing device in the sub-intimal space.
Figure 9A:
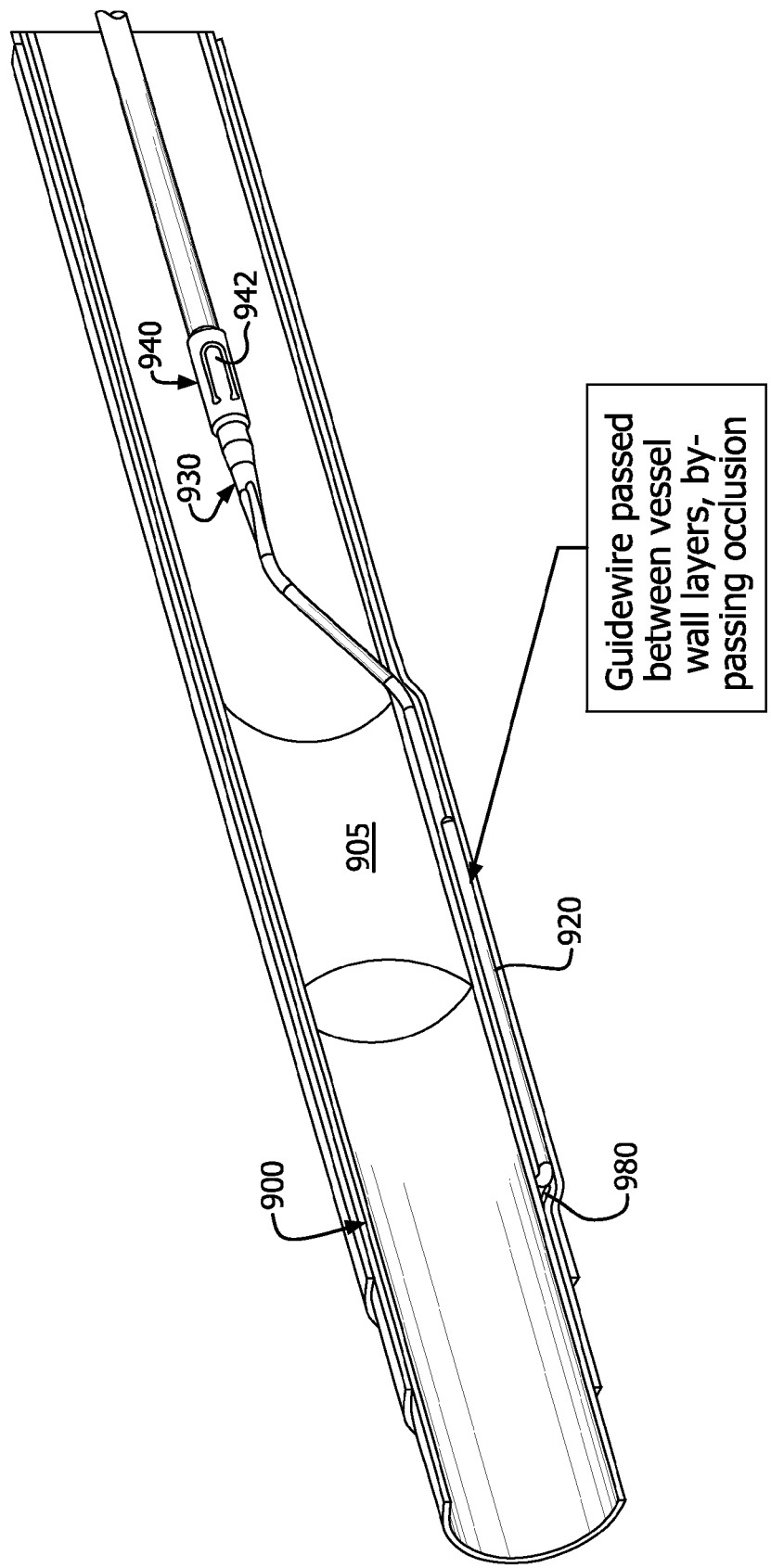
FIG. 9a illustrates an elongate member bypassing the occlusion through sub-intimal dissection.
Figure 9B:
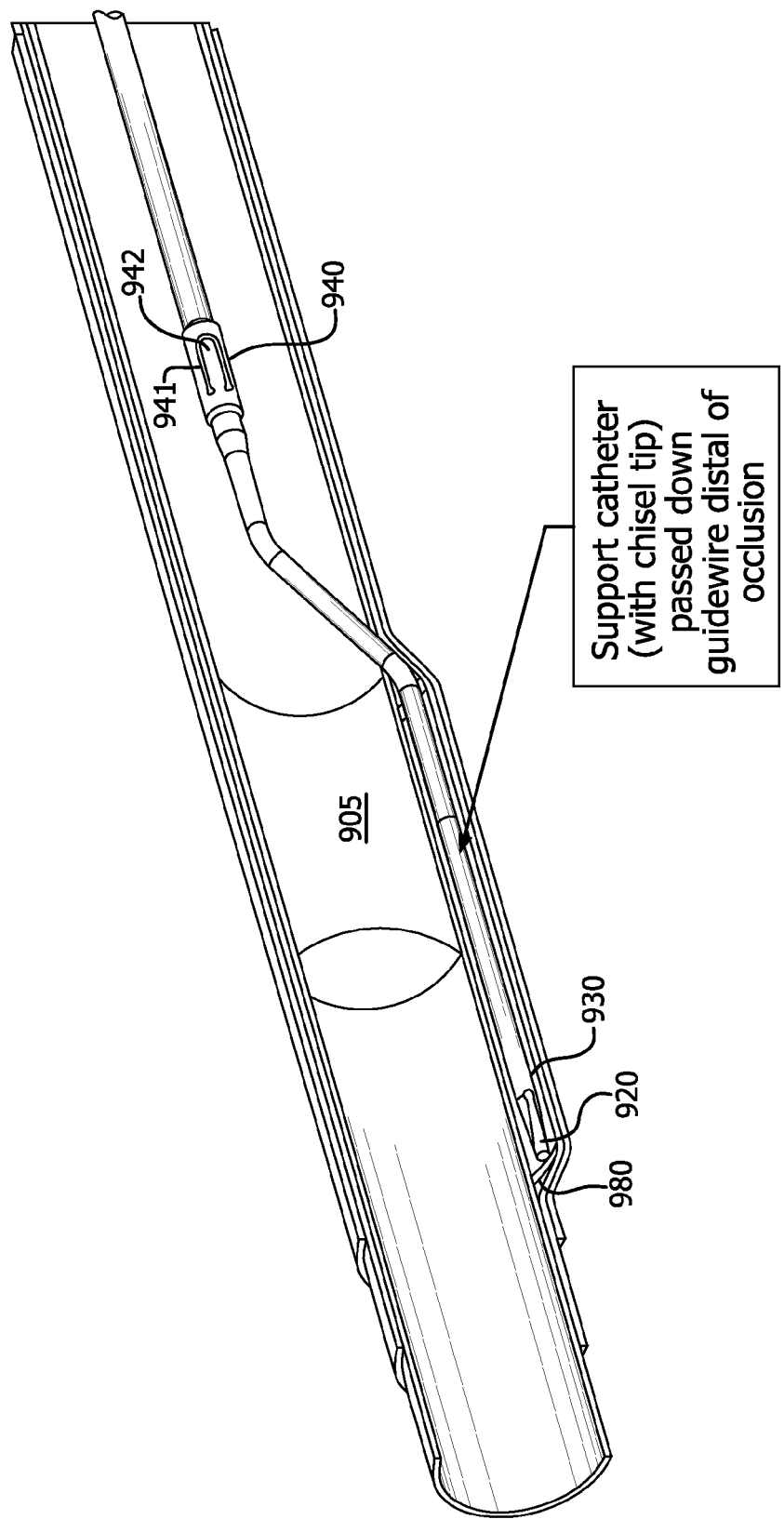
FIG. 9b illustrates the piercing catheter passed down the elongate member distal the occlusion.
Figure 9D:
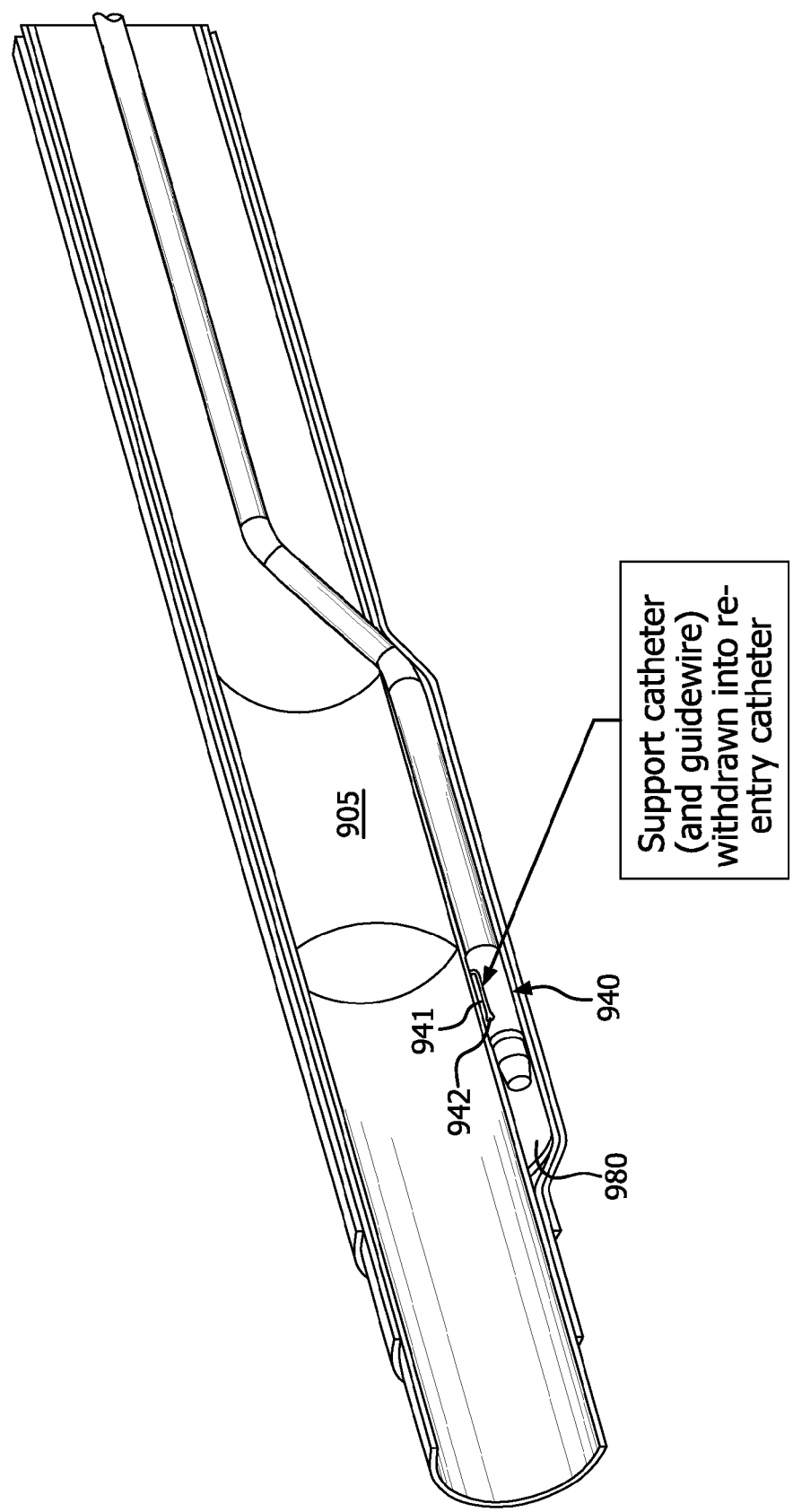
FIG. 9d illustrates the piercing catheter and elongate member retracted into the reentry catheter.
Figure 9E:
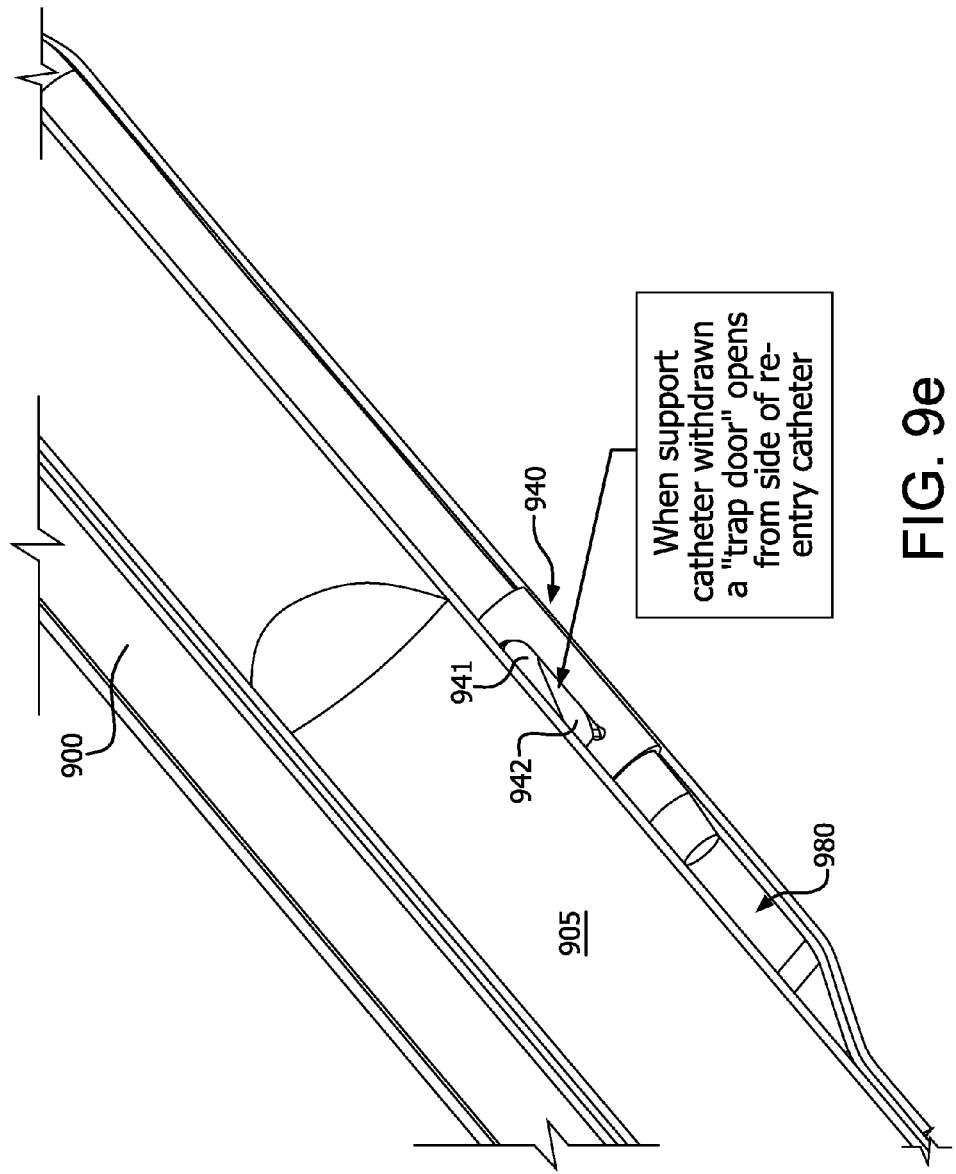
FIG. 9e is an enlarged view of the reentry catheter side-port and illustrates the ramp-door actuated.
Figure 9G:
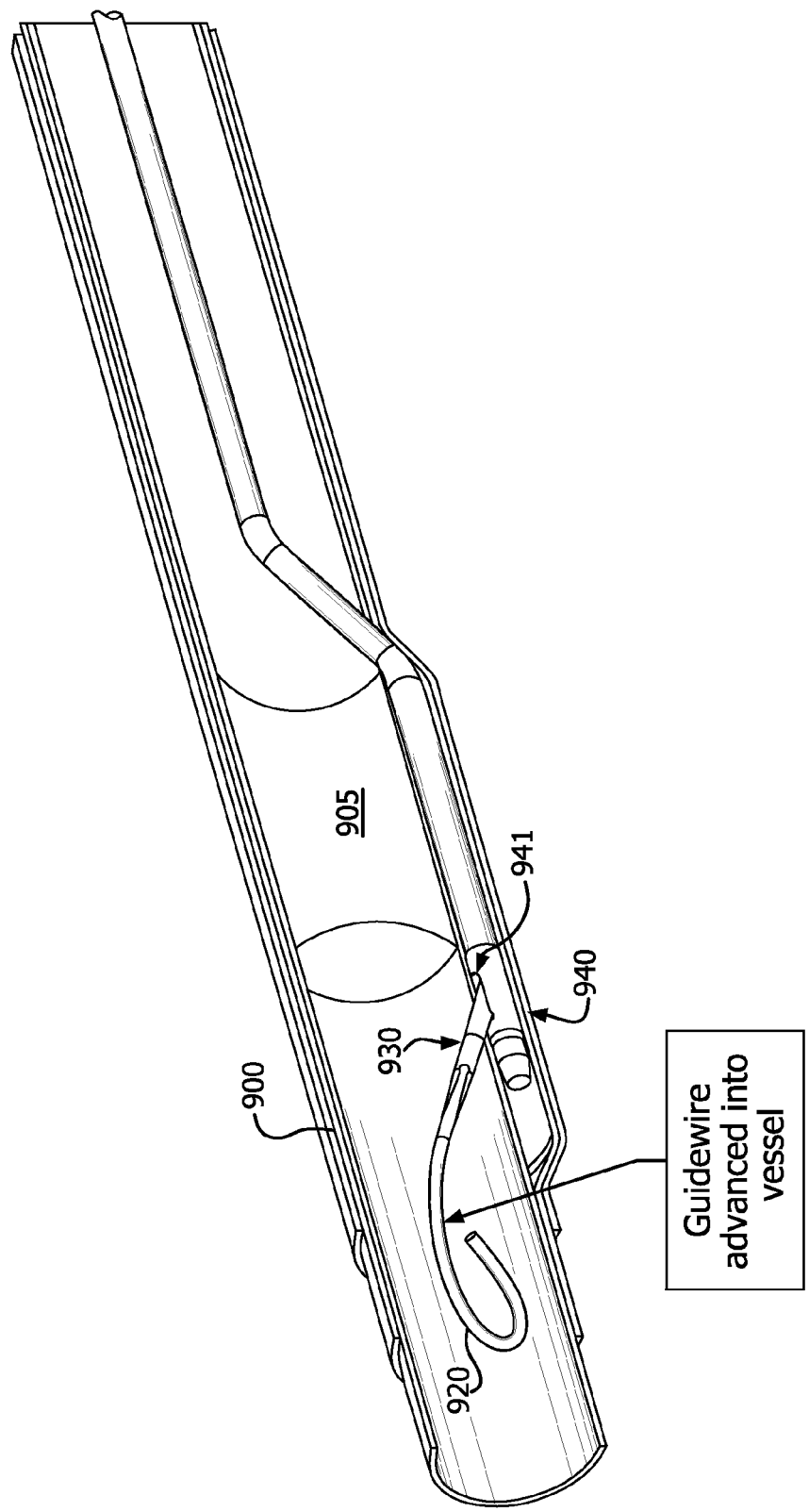
FIG. 9g illustrates an elongate member advanced into the vessel distal the occlusion.
Figure 10:
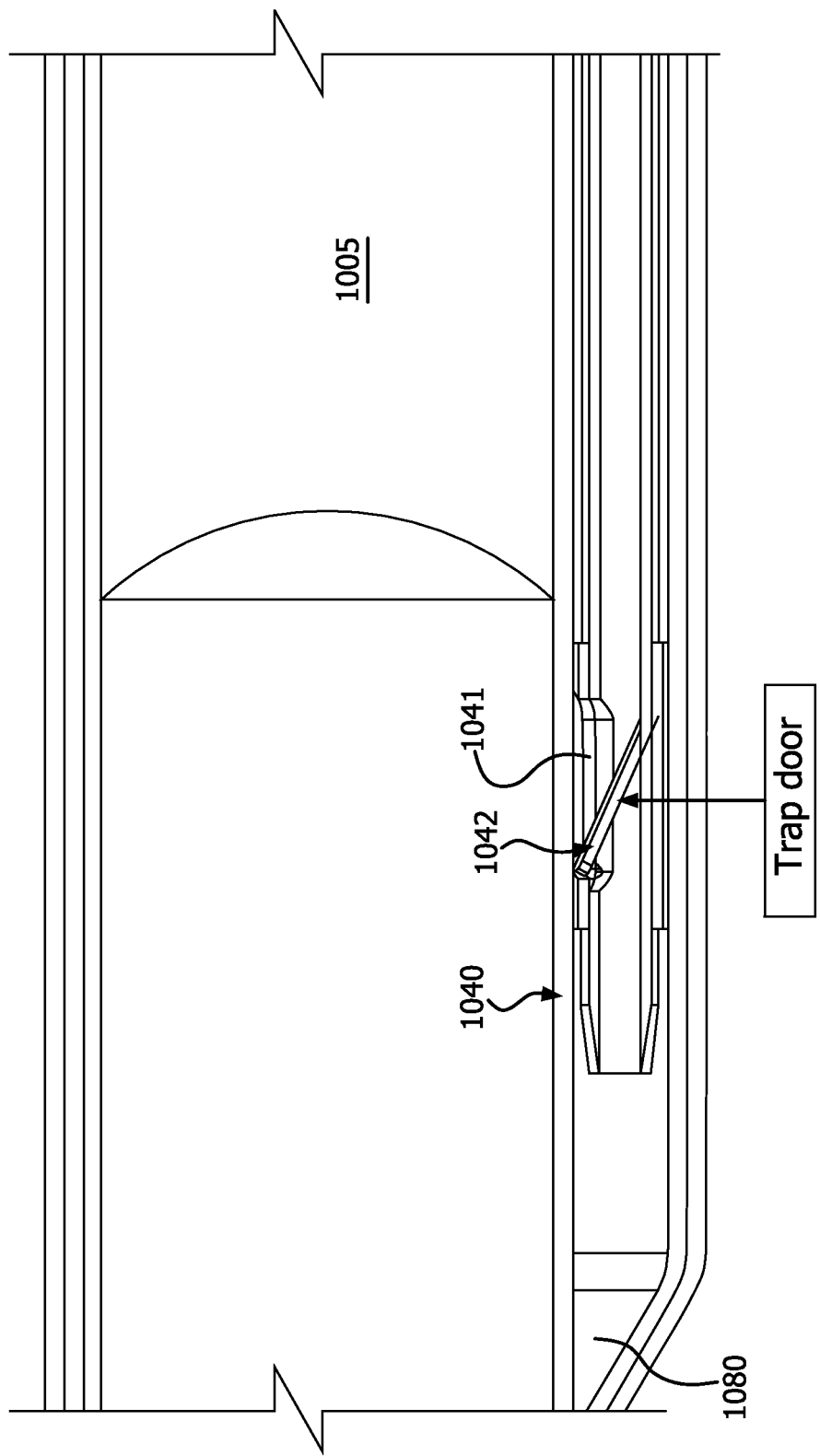
FIG. 10 illustrates a full section view of a reentry catheter showing the ramp-door actuated.
Figure 11A:
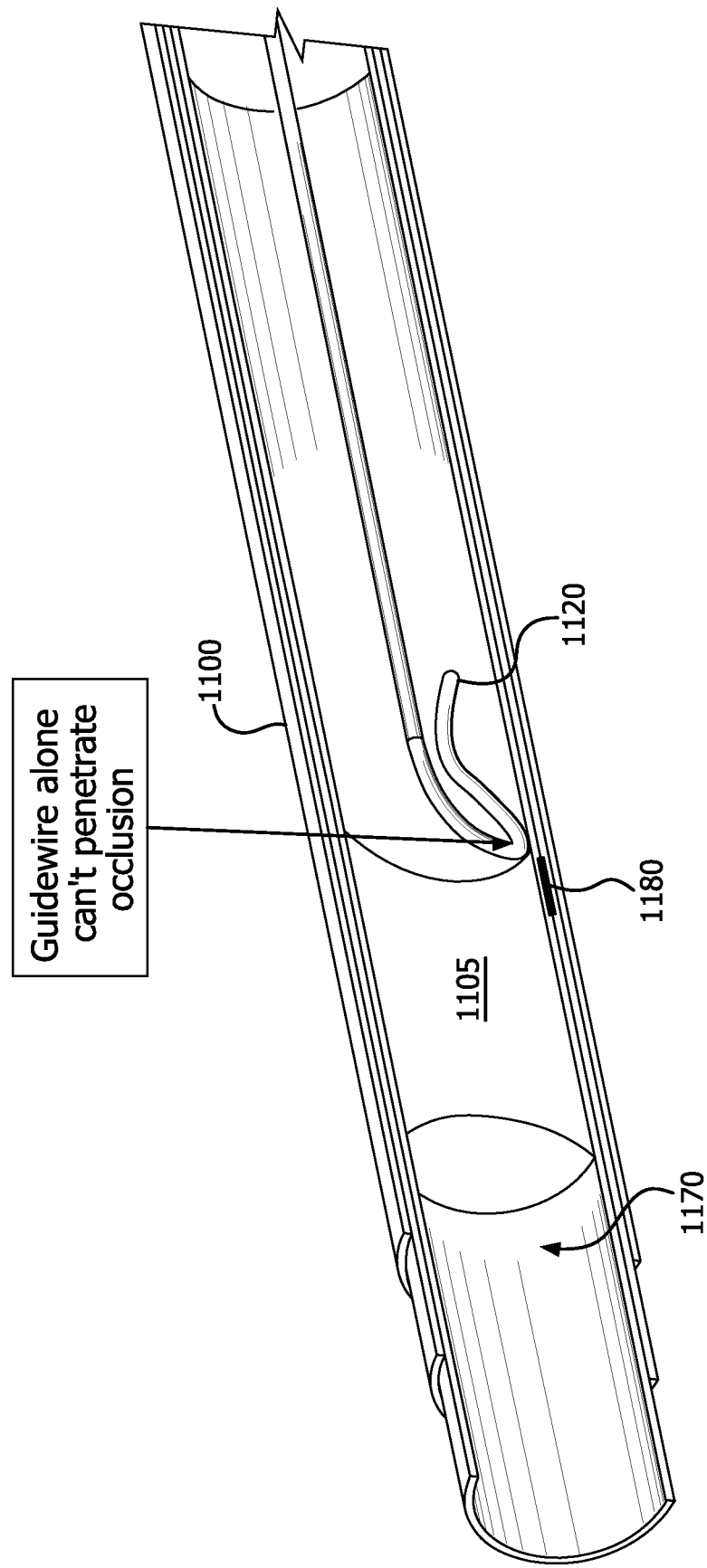
FIGS. 11a-11g illustrate a method and system of bypassing an occlusion with a dual lumen reentry catheter.
Figure 11B:
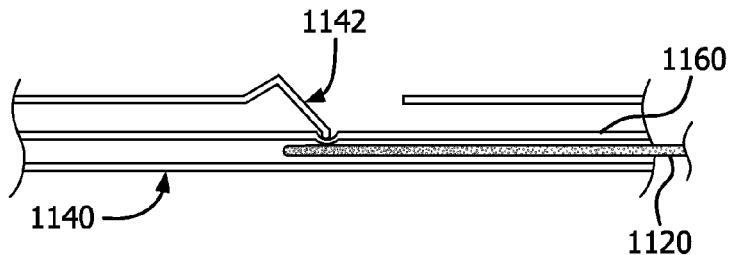
Figure 11C:
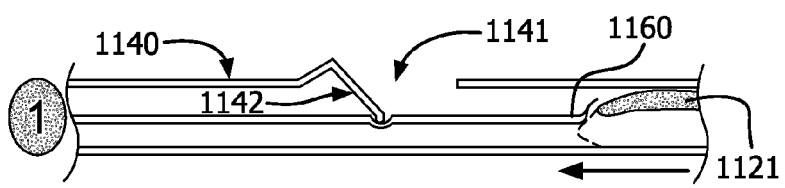
Figure 11D:
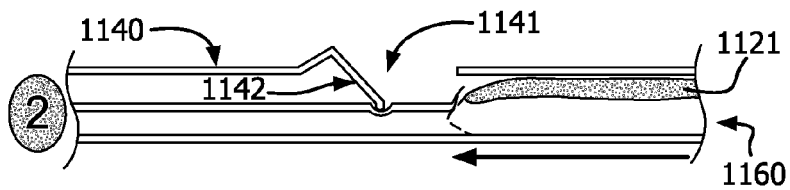
Figure 11E:
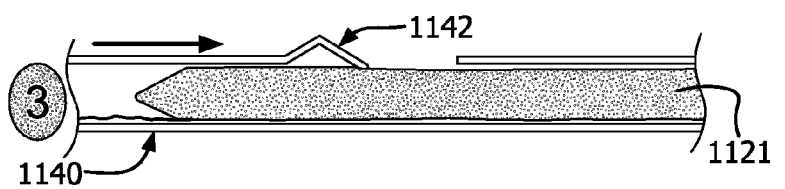
Figure 11F:
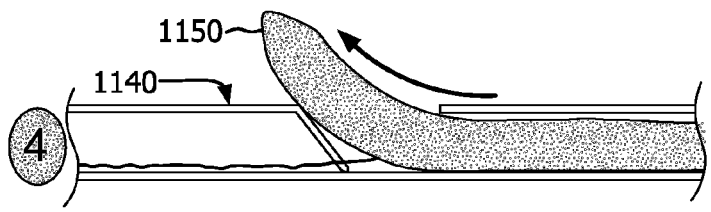
Figure 11G:
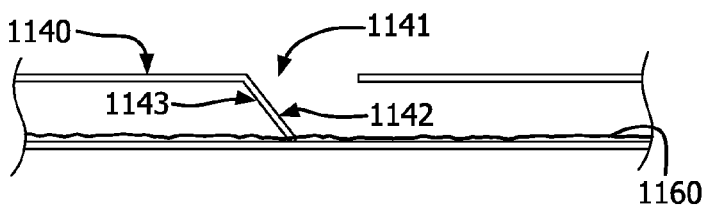

In accordance with exemplary embodiments, and now with reference to FIGS. 8 and 10, a reentry system 850 comprises an elongate member 820 optionally disposed within and moveable along the longitudinal axis and through the lumen of a piercing catheter 830, and a reentry catheter 840. Reentry catheter 840 in turn comprises a side port 841 and a ramp 842, both near its distal end, optionally an outer ring 843, and a hollow member 844, wherein at least one of elongate member 820 and piercing catheter 830 is disposed within and moveable along the longitudinal axis and through the lumen of outer ring 843 and hollow member 844 and can be directed to exit through side port 841 by way of ramp 842. The length between the distal tip of reentry catheter 840 and the distal edge of side port 841 may be varied as clinically required. The stiffness and "torqueability" of reentry catheter 840 may be varied by altering the strength of its materials, the coil configuration (if it is of coiled construction), the braid angle and/or the pick count (if it is of braided construction), and/or by using more or less overwrapping material.

In accordance with various aspects of exemplary embodiments, side-port 841 remains blocked by ramp 842 when at least one of elongate member 820 and piercing catheter 830 is disposed within reentry system 850 and extends distal to side-port 841. When elongate member 820 and piercing catheter 830 are both retracted proximal to side-port 841, ramp 842 is actuated thereby opening side port 841 and presenting ramp 842 to direct reentry of elongate member 820 and piercing catheter 830 back into the lumen of a vessel 800 from the sub-intimal space following sub-intimal dissection. Sub-intimal dissection may be performed by techniques known to those skilled in the art using elongate member 820 or piercing catheter 830. For example, elongate member 820 may comprise a flexible distal end configured to fold over on itself upon meeting resistance from an occlusion 805 and be displaced laterally into the sub-intimal space for sub-intimal dissection.

In exemplary embodiments, ramp 842 is maintained in a blocking configuration by one of elongate member 820 and piercing catheter 830 but is biased to actuate and drop to present itself for directing reentry. Such bias may be accomplished using a shape memory material such as nitinol or any other material or device that permits ramp 842 to drop into its actuated configuration upon the withdrawal of elongate member 820, and piercing catheter 830 when present in exemplary embodiments, from the distal end of reentry catheter 840.

In some embodiments, side port 841 and ramp 842 are integral with hollow member 844. In other embodiments, optional outer ring 843 integrally comprises side port 841 and ramp 842 (e.g., cut from a single tube or formed in a common mold) and circumscribes, or is otherwise coupled to the distal end of, hollow member 844. In accordance with an aspect of an exemplary embodiment comprising a circumscribing outer ring 843, hollow member 844 is configured with its own respective side port on its distal end which is in turn aligned with side port 841. As above, ramp 842 may drop into its actuated configuration upon the withdrawal of elongate member 820, and piercing catheter 830 when present in exemplary embodiments, from the distal end of reentry catheter 840.

In yet other exemplary embodiments, ramp 842 may be pivotally coupled to hollow member 844 within side port 841 to drop into its actuated configuration upon the withdrawal of elongate member 820 and piercing catheter 830 from the distal end of reentry catheter 840. Such embodiments may comprise a spring and/or a hinge.

In various embodiments ramp 842 may be actuated mechanically. For example, ramp may be moved from its closed to open (i.e., angled) position by use of attached pull wires. In another example, ramp 842 may be actuated by axial motion between co-radial inner and outer tubes where one edge or portion of the ramp is attached to one tube and another edge or portion is attached to the other tube. In various embodiments, such relative axial motion could be used to actuate a ramp with spring or memory characteristics whereby the ramp may be formed in the outer tube and upon removal of the inner tube proximate the ramp, the ramp moves into position. In other embodiments, ramp 842 may be moved (or allowed to move) into place by torquing or twisting a co-radial tube assembly. In yet other exemplary embodiments, ramp 842 may comprise an inflatable member, e.g., the ramp is allowed to move into position by either being forced into such position on inflation of a proximally-located bladder or the inverse, i.e., the ramp moves into position by deflation of such a bladder. In various embodiments, ramp 842 may be comprised by the inflatable member itself. In various embodiments, ramp 842 may be actuated hydraulically by directing a stream of fluid (e.g., saline) against some portion of the ramp.

The angle of reentry for devices of the present invention, relative to the longitudinal axis of the reentry catheter 840 (and relative to the longitudinal axis of the vessel), may be varied by design to suit clinician preference. These preferences are typically driven by a clinician's desire to accomplish reentry without piercing the vessel wall across the lumen from the reentry site (a risk when reentry angles are high) and accuracy in reentry at a desired target (a challenge when angles are low). An angle between about 25 to about 50 degrees may be used in certain cases. An angle of between about 35 to about 45 degrees may be used for certain treatment procedures. In another embodiment, said angle is about 25, about 30, about 40, about 45, or about 50 degrees. The angle of reentry may result from one or more design factors. Angle of ramp 842 when moved into position is one such factor but another factor is the flexibility of hollow member 433 (as seen in FIG. 4b) as described above.

The dimensions of reentry catheter 840 should generally be sufficient to permit passage of elongate member 820 and optionally piercing catheter 830.

In exemplary embodiments, reentry catheter 840 is configured to permit passage of an elongate member having an outer diameter of from about 0.010 to about 0.055", more preferably from about 0.025 to about 0.045", and most preferably about 0.040". In exemplary embodiments, the outer diameter of reentry system 850 is from about 0.025 to about 0.10" and more preferably about 0.05".

Figure 12:
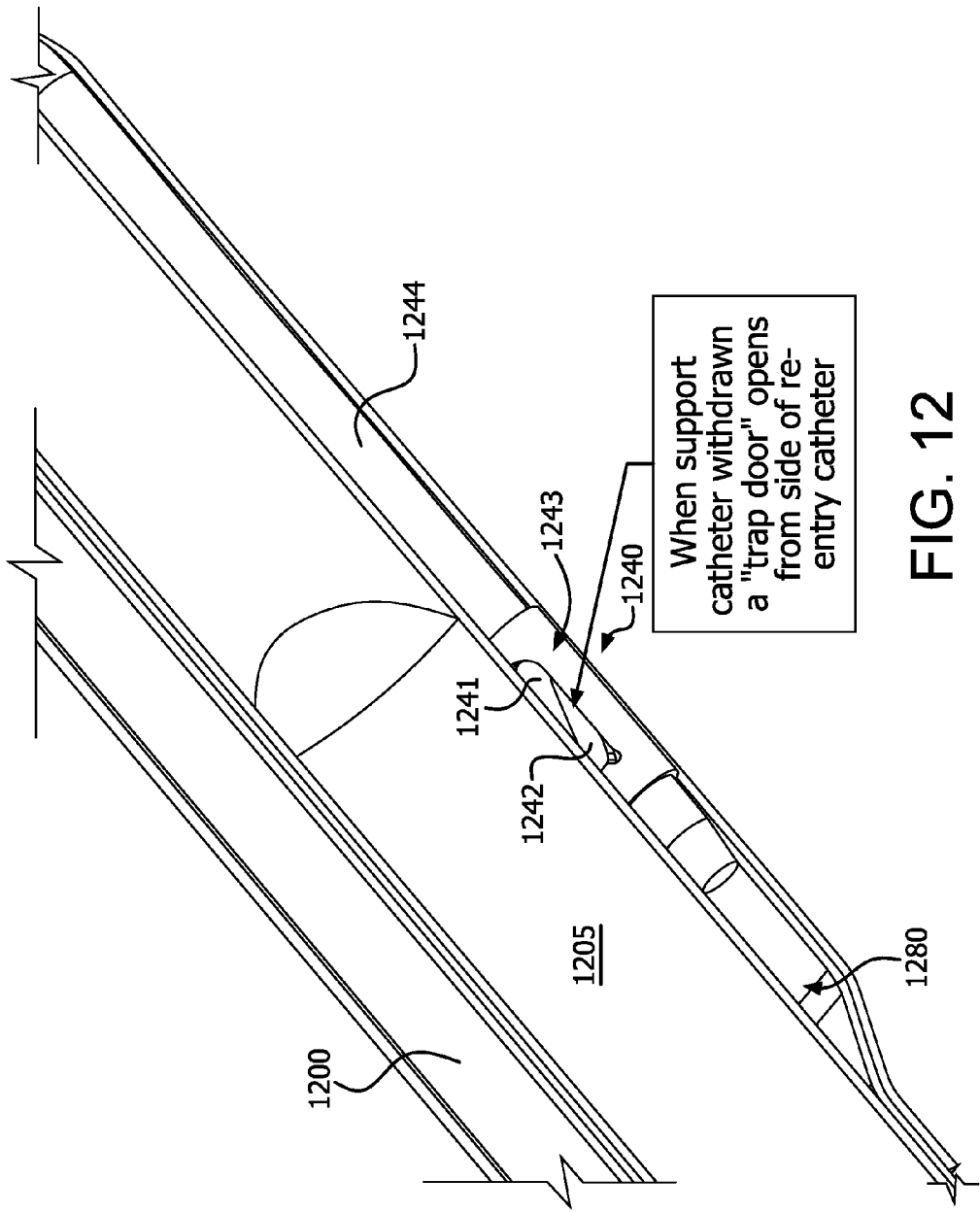
FIG. 12 illustrates a reentry catheter in the sub-intimal space.

As alluded to above, and with momentary reference to FIG. 12, an exemplary reentry system comprises any elongate member, as that term has been defined herein, disposed within and moveable along the longitudinal axis and through the lumen of a reentry catheter 1240. Reentry catheter 1240 in turn comprises a side port 1241 and a ramp 1242, both near its distal end, optionally an outer ring 1243, and a hollow member, wherein the elongate member is disposed within and moveable along the longitudinal axis and through the lumen of outer ring 1243 and hollow member 1244 and can be directed to exit through side port 1241 by way of ramp 1242.

Yet another embodiment of the present invention, and now with reference to FIGS. 11a-11g, comprises a multi-lumen (i.e. dual-lumen) reentry catheter 1140 having a side-port 1141 and a ramp 1142 to guide reentry of an elongate member 1121 from a sub-intimal space 1180 following sub-intimal dissection. In an embodiment, the reentry catheter lumens are separated by a tearable sheath 1160 which supports ramp 1142 in a partially actuated configuration, allowing undisturbed passage of a guidewire 1120 through one of the reentry catheter lumens. Tearable sheath 1160 may be a thin layer of ePTFE or any other tearable material capable of withstanding the downward force of ramp 1142 without tearing. In an embodiment, ramp 1142 is not actuated by withdrawing guidewire 1120 from its respective catheter lumen in a proximal direction past side-port 1141 and ramp 1142. Ramp 1142 is fully actuated by advancing elongate member 1121 sufficient to tear tearable sheath 1160 (due to it having a larger diameter than guidewire 1120) and thereby remove the support for ramp 1142, whereupon elongate member 1121 can be withdrawn to allow full actuation and then advanced through side-port 1141 for reentry into a vessel 1100 from sub-intimal space 1180.

As above, in some embodiments an optional outer ring 1143 integrally comprises side port 1141 and ramp 1142 (e.g., cut from a single tube or formed in a common mold) and circumscribes, or is otherwise coupled to the distal end of, multi-lumen reentry catheter 1140. In accordance with an aspect of an this exemplary embodiment, multi-lumen reentry catheter 1140 is configured with its own respective side port on its distal end which is in turn aligned with side port 1141. Also as above, ramp 1142 may drop into its actuated configuration upon the withdrawal of elongate member 1120, and piercing catheter 1130 when present in exemplary embodiments, from the distal end of multi-lumen reentry catheter 1140.

In an embodiment, a method of using a device such as described herein comprises the steps of inserting an elongate member into an occluded vessel proximate an occlusion; advancing a piercing catheter over the elongate member to a position proximate the distal end of the elongate member; and applying a longitudinal force to advance the elongate member into the occlusion.

In various embodiments, when the piercing catheter is proximal to the elongate member, it serves to support the elongate member so that it has sufficient stiffness to cross the occlusion.

Figure 5B:
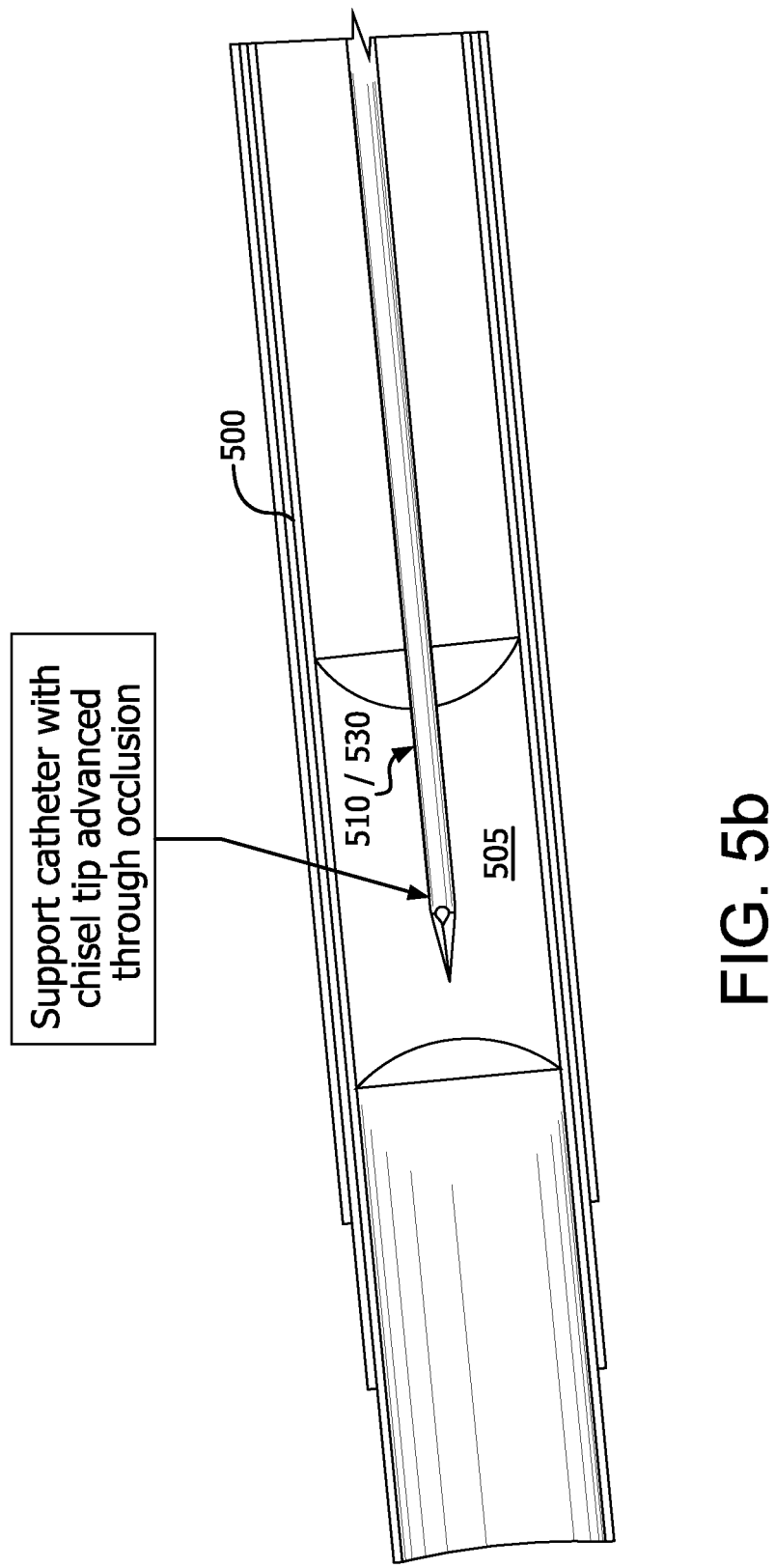
Figure 5C:
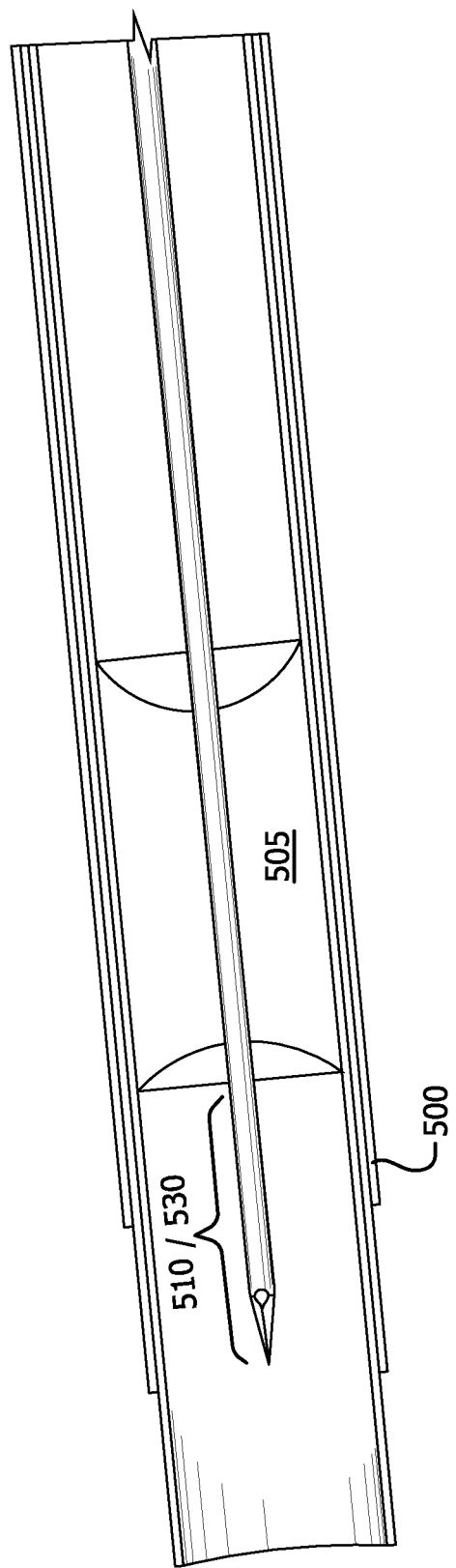

In accordance with another embodiment and with reference to FIGS. 5a through 5c, a method comprises the steps of inserting an elongate member 520 into an occluded vessel proximate an occlusion 505; advancing a piercing catheter 530 over the elongate member 520 to a position beyond the distal end of the elongate member 520 such that a tip 532 is formed at the distal end of the piercing catheter 530, and applying a longitudinal force to advance the piercing catheter 530 into the occlusion 505. A further embodiment involves reciprocating the elongate member 520 in and out of the chisel's 531 distal end to actuate the chisel 531 between an open tip (See FIG. 6) and closed tip (See FIG. 4a) as the piercing catheter 530 is advanced into the occlusion 505. In another embodiment, tip 532 is used to pierce the fibrous cap of the occlusion then elongate member 520 (i.e. a guidewire) is pushed through the rest of the occlusion.

In accordance with another embodiment and with reference to FIGS. 9a-9g, the present invention comprises the steps of inserting an elongate member 920 into an occluded vessel 900 proximate an occlusion 905; advancing the elongate member 920 into the sub-intimal space 980 of the occluded vessel 900 so the distal end of the elongate member 920 has bypassed the occlusion 905; advancing a piercing catheter 930 over the elongate member 920 to a position proximate the distal end of the elongate member 920; advancing a reentry catheter 940 over the piercing catheter 930; retracting the elongate member 920 and piercing catheter 930 to actuate the ramp 942 and; applying a longitudinal force to advance the piercing catheter 930 up the ramp 942 to re-enter the occluded vessel 900 on the distal side of the occlusion 905.

In accordance with an exemplary embodiment and with reference to FIG. 11a-11f, the present invention comprises the steps of inserting a guidewire 1120 into an occluded vessel 1100 proximate an occlusion 1105; advancing the guidewire into the sub-intimal space 1180 of the occluded vessel 1105 so the distal end 1170 of the elongate member 1120 has bypassed the occlusion 1105; advancing a reentry catheter 1140 with a tearable sheath 1160 over the elongate member 1120 so that the reentry catheter's 1140 distal end is proximate the distal end of the elongate member 1120; withdrawing the guidewire 1120; advancing a larger elongate member 1121 distal the side-port and thereby tearing the tearable sheath 1160; withdrawing the larger elongate member 1121 proximal the side-port 1141 and thereby actuating the ramp 1142; and applying a longitudinal force to advance the larger elongate member 1121 up the ramp 1142 to re-enter the occluded vessel 1100 on the distal side 1170 of the occlusion 1105. The larger elongate member 1121 could be a piercing catheter (See embodiment 310).

And yet another exemplary embodiment comprises the steps of applying a longitudinal force to advance a piercing catheter through any anatomical feature, wherein the piercing catheter comprises: an elongate member; a hollow chisel with proximal and distal ends, wherein the distal end actuates between an open and closed position; wherein the distal end opens when the elongate member passes through the distal end; and wherein the distal end closes to form the tip when the elongate member is removed from the distal end; and a catheter with its distal end attached to the chisel's proximate end such that the catheter and the chisel circumscribe the elongate member.

And yet another exemplary method comprises an attempted crossing of an occlusion through the lumen of the occluded vessel and abandoning the cross approach and instead performing a sub-intimal dissection to bypass the occlusion. An embodiment may comprise inserting an elongate member into an occluded vessel proximate an occlusion; advancing a piercing catheter over the elongate member to a position beyond the distal end of the elongate member such that a tip is formed at the distal end of the piercing catheter; applying a longitudinal force to advance the piercing catheter into the occlusion; withdrawing the piercing catheter proximal the distal end of the elongate member; advancing the elongate member into the sub-intimal space of the occluded vessel distal the occlusion; advancing a piercing catheter over the elongate member to a position proximate the distal end of the elongate member; advancing a reentry catheter over the piercing catheter, retracting the elongate member and piercing catheter to actuate the ramp; and applying a longitudinal force to advance the piercing catheter up the ramp to re-enter the occluded vessel on the distal side of the occlusion.

In various embodiments, catheters, piercing catheters, reentry catheters and the like referenced herein may incorporate any of the various aspects described. Moreover, other embodiments comprise using devices and methods described herein to perforate and exit the vessel completely through the perforation site and creating a bypass in neighboring vessel or tissue. Other embodiments comprise using devices and methods described herein to pierce grafts or stent-grafts to create fenestrations. Fenestrations to host vessels and/or indwelling devices (grafts and stent-grafts) could be facilitated with this system. The flexible nature of the puncturing tool allows for easy and accurate deflection from the host lumen to the vessel wall. Forward axial deflection would then cause the puncturing tool to pierce the endoprosthesis and/or vessel. Continued forward movement would allow the puncturing tool to traverse tissue and possible even re-enter another vessel lumen for a specific purpose such as constructing an A-V Fistula or a TIPS procedure. In one embodiment, said medical device has a method of buttressing said device against a vessel, stent and/or stent-graft in order to generate enough force to pierce said vessel, stent, and/or stent-graft.

Traversing tissue may require the clinician to use some mode of imaging (Ultrasound/Angiography, in which case, the puncturing tool would be configured to be echogenic or radiopaque. Still other embodiments may include various coatings to the various structures described herein, such as for example, ePTFE, Heparin, or the like.

In another embodiment, the medical device of the invention may comprise an echogenic and/or radio-opaque material permitting visualizing by medical imagery, particularly by ultrasound and/or radiography, the position of the medical device of the invention. The echogenic portion includes an echogenic material comprising a plastic impregnated with sonically reflective particles.

Radiopaque markers or similar indicia are often used to allow the medical staff to exactly position the medical device using the imagining technology. The system of the invention may include some type of radiopaque marker to allow the physician performing the procedure to monitor the progress of the system through the body. The system may contain either radiopaque markers or contain radiopaque materials commonly known in the art. The markings may also include a radiopaque material to aid in non-invasive visualization or other suitable visualization materials as known in the art. In addition, one or more radiopaque metallic fibers, such as gold, platinum, platinum-tungsten, palladium, platinum-iridium, rhodium, tantalum, or alloys or composites of these metals like may be incorporated into the device, particularly, into the graft, to allow fluoroscopic visualization of the device.

Features of the known art that could be incorporated into the present invention(s) include steerable catheter(s) and the use of a contrast agent delivered through the support catheter's lumen to confirm reentry.

The systems and methods described herein may be useful in connection with the treatment of coronary artery disease, peripheral vascular diseases, portal hypertension, carotid artery disease, renal vascular hypertension, occlusion of the iliac vessels, subintimal angioplasty (as described in Bolia, et al. Cardiovasc. Intervent. Radiol., 13, 357-363, (1990)), biopsies, and in situ fenestration of other tissues, amongst other conditions affecting anatomical conduits. The present invention may also be useful to pierce grafts or stent-grafts to create fenestrations and to create anatomical passages such as an arterio-venous fistula.

The foregoing disclosure is merely illustrative of the present invention and is not intended to be construed as limiting the invention. Although one or more embodiments of the present invention have been described, persons skilled in the art will readily appreciate that numerous modifications could be made without departing from the spirit and scope of the present invention. As such, it should be understood that all such modifications are intended to be included within the scope of the present invention.

We claim:

1. A medical device system comprising:
   a catheter with proximal and distal ends;
   a hollow chisel having a chisel passage therein, having a proximal and distal end, with a tip at the distal end, wherein the chisel's proximal end is proximate to the catheter's distal end; and
   an elongate member axially movable along the longitudinal axis of the catheter and chisel, where in the elongate member is a guidewire, a catheter, or fiber;
   wherein the tip is movable, in response to selective axial displacement of the elongate member, between a first position, in which the tip is disposed proximal to the axis, and a second position, in which the tip is spaced apart from the first position.

2. The medical device system of claim 1, wherein the tip has at least two portions, at least one of which is moveable in response to selective axial displacement of the elongate member.

3. The medical device system of claim 2, wherein when the elongate member is withdrawn out of the chisel passage, a sharp tip forms.

4. The medical device system of claim 1, wherein the elongate member can be reciprocated in and out of the chisel's distal end to actuate the chisel between a sharp tip and a blunt tip.

5. The medical device system of claim 1, wherein when the elongate member is pushed through and out of the distal end of the chisel, the tip opens to generally conform to the outer diameter of the elongate member.

6. The medical device system of claim 1, wherein when the elongate member is pushed out of the distal end of the chisel, the catheter and chisel together comprise a support catheter.

7. The medical device system of claim 1, wherein the chisel comprises a shape memory material.

8. The medical device system of claim 7, wherein the shape memory material is nitinol.

* * * * *